United States Patent [19]
Georgiou

[11] Patent Number: 5,866,344
[45] Date of Patent: Feb. 2, 1999

[54] ANTIBODY SELECTION METHODS USING CELL SURFACE EXPRESSED LIBRARIES

[75] Inventor: George Georgiou, Austin, Tex.

[73] Assignee: Board of Regents, The University of Texas System, Austin, Tex.

[21] Appl. No.: 447,402

[22] Filed: May 23, 1995

Related U.S. Application Data

[60] Continuation-in-part of Ser. No. 258,543, Jun. 10, 1994, abandoned, which is a division of Ser. No. 794,731, Nov. 15, 1991, Pat. No. 5,348,867.

[51] Int. Cl.$^6$ .................................................. G01N 33/554
[52] U.S. Cl. ........................ 435/7.21; 435/7.1; 435/7.32
[58] Field of Search ..................................... 436/518, 519; 435/7.1

[56] References Cited

U.S. PATENT DOCUMENTS

| | | | |
|---|---|---|---|
| 4,035,074 | 7/1977 | Lem ............................................ | 424/1 |
| 4,166,767 | 9/1979 | Kurooka et al. ............................ | 435/7 |
| 4,496,658 | 1/1985 | Kondo et al. ............................ | 436/510 |
| 5,348,867 | 9/1994 | Georgiou et al. ....................... | 435/69.7 |

OTHER PUBLICATIONS

Charbit A, et al, (1991) Permissive sites and topology of an outer membrane protein with a reporter epitope. J. Bacteriol. 173:262–275.

Huse WD, et al, (1989) Generation of a large combinatorial library of the immunoglobulin repertoire in phage lambda. Science 246:1275–1281.

Jonsson S, Kronvall G, (1974) The use of protein A containing Staphylococcus aureus as a solidphase anti IgG reagent in radioimmunoassays as exemplified in the quantitation of alpha fetoprotein in normal adult serum. Eur.J.Immunol. 4:29–33.

Kessler SW, (1975) Rapid isolation of antigens from cells with a staphylococcal protein A–antibody adsorbent: parameters of the interaction of antibody–antigen complexes with protein A. J. Immunol. 115:1617–1624.

McCafferty J. Griffiths AD, et al, (1990) Phage antibodies: filamentous phage displaying antibody variable domains. Nature 348:552–554.

Aiyar and Leis, "Modification of the Megaprimer Method of PCR Mutagenesis: Improved Amplification of the Final Product," *BioTechniques*, 14(3):366, 1993.

Barbas III et al., "Assembly of combinatorial antibody libraries on phage surfaces: The gene III site," *Proc. Natl. Acad. Sci. USA*, 88:7978–7982, Sep. 1991.

Barbas III et al., "Semissynthetic combinatorial antibody libraries: A chemical solution tothe diversity problem," *Proc. Natl. Acad. Sci. USA*, 89:4457–4461, May 1992.

Clackson et al., "Making antibody fragments using phage display libraries," *Nature*, 352:624–628, Aug. 1991.

Francisco et al., Transport and achoring of β–lactamase to the external surface of *Escherichia coli*, *Proc. Natl. Acad. Sci. USA*, 89:2713–2717, Apr. 1992.

Francisco et al., "Production and fluorescence–activated cell sorting of *Escherichia coli* expressing a functional antibody fragment on the external surface," *Proc. Natl. Acad. Sci. USA*, 90:10444–10448, Nov. 1993.

Georgious et al., "Folding and aggregation of β–lactamase: Analogies with the formation of inclusion bodies in *Escherichia coli*," *Protein Science*, 3:1953–1960, 1994.

Iverson et al., "A Combinatorial System for Cloning and Expressing the Catalytic Antibody Repertoire in *Escherichia coli*," *Cold Spring Harbor Symposia on Quantitative Biology*, vol. LIV., 273–280. 1989.

Persson et al., "Generation of diverse high–affinity human monoclonal antibodies by repertoire cloning," *Proc. Natl. Acad. Sci. USA*, 88:2432–2436, Mar. 1991.

Sastry et al., "Cloning of the immunological repertoire in *Escherichia coli* for generation of monoclonal catalytic antibodies: Construction of a heavy chain variable region–specific cDNA library," *Proc. Natl. Acad. Sci. USA*, 86:5728–5732, Aug. 1989.

Schildbach et al., "Modulation of antibody affinity by a non–contact residue," *Protein Science*, 2:206–214, 1993.

Yang et al., Electrochemiluminescence: A New Diagnostic and Research Tool, *Bio/Technology*, 12:193–194, Feb. 1994.

*Primary Examiner*—Lora M. Green
*Assistant Examiner*—Neal A. Musto
*Attorney, Agent, or Firm*—Arnold, White & Durkee

[57] ABSTRACT

The invention relates to novel competitive immunoassays that are useful in detecting and quantitatively measuring analytes down to the nanomolar range. The invention also includes methods of selecting antibodies from libraries of polypeptides expressed on a cell surface. In conducting immunoassays, anti-analyte antibody molecules are expressed on the surface of a bacterial cell and then used to bind with labeled analyte. Quantitation is performed by competitively displacing the bound labeled analyte with a known amount of analyte and measuring the label. The method is rapid and inexpensive and may be performed with readily available safe labeling reagents such as fluorescent compounds.

4 Claims, 12 Drawing Sheets

Variable Heavy Chain

| Glu | Val | Gln | Leu | Gln | Gln | Ser | Gly | Pro | Glu | Leu | Val | Lys | Pro | Gly | Ala | Ser | Val | Arg | Met | Ser |
|-----|-----|-----|-----|-----|-----|-----|-----|-----|-----|-----|-----|-----|-----|-----|-----|-----|-----|-----|-----|-----|
| GAA | GTT | CAA | CTG | CAA | CAG | TCT | GGT | CCT | GAA | TTG | GTT | AAA | CCT | GGC | GCC | TCT | GTG | CGC | ATG | TCC |

| Cys | Lys | Ser | Ser | Gly | Tyr | Ile | Phe | Thr | Asp | Phe | Tyr | Met | Asn | Trp | Val | Arg | Gln | Ser | His | Gly |
|-----|-----|-----|-----|-----|-----|-----|-----|-----|-----|-----|-----|-----|-----|-----|-----|-----|-----|-----|-----|-----|
| TGC | AAA | TCC | TCA | GGG | TAC | ATT | TTC | ACC | GAC | TTC | TAC | ATG | AAT | TGG | GTT | CGC | CAG | TCT | CAT | GGT |

| Lys | Ser | Leu | Asp | Tyr | Ile | Gly | Tyr | Ile | Ser | Pro | Tyr | Ser | Gly | Val | Thr | Gly | Tyr | Asn | Gln | Lys |
|-----|-----|-----|-----|-----|-----|-----|-----|-----|-----|-----|-----|-----|-----|-----|-----|-----|-----|-----|-----|-----|
| AAG | TCT | CTA | GAC | TAC | ATC | GGG | TAC | ATT | TCC | CCA | TAC | TCT | GGG | GTT | ACC | GGC | TAC | AAC | CAG | AAG |

| Phe | Lys | Gly | Lys | Ala | Thr | Leu | Thr | Val | Asp | Lys | Ser | Ser | Ser | Thr | Ala | Tyr | Met | Glu | Leu | Arg |
|-----|-----|-----|-----|-----|-----|-----|-----|-----|-----|-----|-----|-----|-----|-----|-----|-----|-----|-----|-----|-----|
| TTT | AAA | GGT | AAG | GCC | ACC | CTT | ACT | GTC | GAC | AAA | TCT | TCC | TCA | ACT | GCT | TAC | ATG | GAG | CTG | CGT |

| Ser | Leu | Thr | Ser | Glu | Asp | Ser | Ala | Val | Tyr | Tyr | Cys | Ala | Gly | Ser | Ser | Gly | Asn | Lys | Trp | Ala |
|-----|-----|-----|-----|-----|-----|-----|-----|-----|-----|-----|-----|-----|-----|-----|-----|-----|-----|-----|-----|-----|
| TCT | TTG | ACC | TCT | GAG | GAC | TCC | GCG | GTA | TAC | TAT | TGC | GCC | GGC | TCC | TCT | GGT | AAC | AAA | TGG | GCC |

Linker

| Met | Asp | Tyr | Trp | Gly | His | Gly | Ala | Ser | Val | Thr | Val | Ser | Ser | Gly | Gly | Gly | Gly | Ser | Gly | Gly |
|-----|-----|-----|-----|-----|-----|-----|-----|-----|-----|-----|-----|-----|-----|-----|-----|-----|-----|-----|-----|-----|
| ATG | GAT | TAT | TGG | GGT | CAT | GGT | GCT | AGC | GTT | ACT | GTG | AGC | TCT | GGT | GGC | GGT | GGC | TCG | GGC | GGT |

FIG. 1A

Variable Light Chain

| Gly | Gly | Ser | Gly | Gly | Gly | Ser | Asp | Val | Val | Met | Thr | Gln | Thr | Pro | Leu | Ser | Leu | Pro | Val |
|---|---|---|---|---|---|---|---|---|---|---|---|---|---|---|---|---|---|---|---|
| GGT | GGG | TCG | GGT | GGC | GGA | TCA | GAC | ATA | GTA | CTG | ACC | CAG | TCT | CCA | GCT | TCT | TTG | GCT | GTG |

| Ser | Leu | Gly | Asp | Gln | Ala | Ser | Ile | Ser | Cys | Arg | Ser | Ser | Gln | Ser | Leu | Val | His | Ser | Asn | Gly |
|---|---|---|---|---|---|---|---|---|---|---|---|---|---|---|---|---|---|---|---|---|
| TCT | CTA | GGA | CAA | AGG | GCC | TCC | ATA | TCC | TGC | CGA | TCC | AGC | CAA | AGT | CTC | GTA | CAT | TCT | AAT | GGT |

| Asn | Thr | Tyr | Leu | Asn | Trp | Tyr | Leu | Gln | Lys | Ala | Gly | Gln | Ser | Pro | Lys | Leu | Leu | Ile | Tyr | Lys |
|---|---|---|---|---|---|---|---|---|---|---|---|---|---|---|---|---|---|---|---|---|
| AAT | ACT | TAT | CTG | AAC | TGG | TAC | CAA | CAG | AAA | GCC | GGA | CAG | CCA | CCC | AAG | CTT | CTC | ATC | TAT | AAG |

| Val | Ser | Asn | Arg | Phe | Ser | Gly | Val | Pro | Asp | Arg | Phe | Ser | Gly | Ser | Gly | Ser | Gly | Ser | Asp | Phe |
|---|---|---|---|---|---|---|---|---|---|---|---|---|---|---|---|---|---|---|---|---|
| GTA | TCC | AAC | CGA | TTC | TCT | GGA | GTC | CCT | GCC | AGG | TTC | AGT | GGC | AGT | GGG | TCT | GAG | TCA | GAC | TTC |

| Thr | Leu | Thr | Ile | Asp | Pro | Val | Glu | Glu | Asp | Asp | Ala | Ala | Ile | Tyr | Tyr | Cys | Ser | Gln | Thr | Thr |
|---|---|---|---|---|---|---|---|---|---|---|---|---|---|---|---|---|---|---|---|---|
| ACC | CTC | ACC | ATC | GAT | CCT | GTG | GAG | GAG | GAT | GAT | GCT | GCA | ATA | TAT | TAC | TGT | AGC | CAA | ACT | ACG |

| His | Val | Pro | Pro | Thr | Phe | Gly | Ser | Gly | Thr | Lys | Leu | Glu | Leu | Lys | Pro | Ala | Ser | Gln | Pro | Glu |
|---|---|---|---|---|---|---|---|---|---|---|---|---|---|---|---|---|---|---|---|---|
| CAT | GTT | CCA | CCC | ACG | TTC | GGC | TCG | GGG | ACC | AAG | CTG | GAG | CTG | AAA | CGT | GCT | AGC | CAG | CCA | GAA |

HSV

| Leu | Ala | Pro | Glu | Asp | Pro | Glu | Asp |
|---|---|---|---|---|---|---|---|
| CTC | GCC | CCG | GAA | GAC | CCC | GAG | GAC |

(SEQ ID NO: 1)
(SEQ ID NO: 6)

FIG. 1B

Primer #1
5'- CAG AGT GCC ATG ACC CCA ATA ATC XXX GGC XXX TTT
    GTT ACC AGA XXX GCC GGC -3' (SEQ ID NO: 2)

Primer #2
5'- CA GGG TAC ATT TTC ACC GAC TTC XXX ATG AAT TTG -3' (SEQ ID NO: 3)

Primer #3
5'- C GGT GAA AAT GTA CCC TG -3' (SEQ ID NO: 4)

Primer #4
5'- TGG ACC AAC AAC ATC -3' (SEQ ID NO: 5)

FIG. 5

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 260 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Glu Val Gln Leu Gln Gln Ser Gly Pro Glu Leu Val Lys Pro Gly Ala
 1               5                  10                  15

Ser Val Arg Met Ser Cys Lys Ser Ser Gly Tyr Ile Phe Thr Asp Phe
            20                  25                  30

Tyr Met Asn Trp Val Arg Gln Ser His Gly Lys Ser Leu Asp Tyr Ile
            35                  40                  45

Gly Tyr Ile Ser Pro Tyr Ser Gly Val Thr Gly Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly Gly
            115                 120                 125

Ser Gly Gly Gly Gly Ser Asp Ile Val Leu Thr Gln Ser Pro Ala Ser
    130                 135                 140

Leu Ala Val Ser Leu Gly Gln Arg Ala Thr Ile Ser Cys Arg Ser Ser
```

```
145                    150                    155                      160
Gln  Ser  Leu  Val  His  Ser  Asn  Gly  Asn  Thr  Tyr  Leu  Asn  Trp  Tyr  Gln
                    165                    170                    175
Gln  Lys  Pro  Gly  Gln  Pro  Pro  Lys  Leu  Leu  Ile  Tyr  Lys  Val  Ser  Asn
               180                    185                    190
Arg  Phe  Ser  Gly  Val  Pro  Ala  Arg  Phe  Ser  Gly  Ser  Gly  Ser  Glu  Ser
               195                    200                    205
Asp  Phe  Thr  Leu  Thr  Ile  Asp  Pro  Val  Glu  Glu  Asp  Ala  Ala  Ile
     210                    215                    220
Tyr  Tyr  Cys  Ser  Gln  Thr  Thr  His  Val  Pro  Pro  Thr  Phe  Gly  Ser  Gly
225                    230                    235                         240
Thr  Lys  Leu  Glu  Leu  Lys  Arg  Ala  Ser  Gln  Pro  Glu  Leu  Ala  Pro  Glu
                    245                    250                    255
Asp  Pro  Glu  Asp
               260
```

( 2 ) INFORMATION FOR SEQ ID NO:2:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 25..27
        ( D ) OTHER INFORMATION: /mod_base=OTHER
            / note= "N= C, A, G, or T"

( i x ) FEATURE:
        ( A ) NAME/KEY: modified_base
        ( B ) LOCATION: 31..33
        ( D ) OTHER INFORMATION: /mod_base=OTHER
            / note= "N= C, A, G, or T"

( i x ) FEATURE:
        ( A ) NAME/KEY: modified_base
        ( B ) LOCATION: 46..48
        ( D ) OTHER INFORMATION: /mod_base=OTHER
            / note= "N = C, A, T, or G"

( x i ) SEQUENCE DESCRIPTION: SEQ ID NO:2:

CAGAGTGCCA TGACCCCAAT AATCNNNGGC NNNTTTGTTA CCAGANNNGC CGGC    54

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 24..26
        ( D ) OTHER INFORMATION: /mod_base=OTHER
            / note= "N = G, A, C, or T"

( x i ) SEQUENCE DESCRIPTION: SEQ ID NO:3:

CAGGGTACAT TTTCACCGAC TTCNNNATGA ATTGG    35

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single -continued ( D ) TOPOLOGY: linear ( x i ) SEQUENCE DESCRIPTION: SEQ ID NO:4:

CGGTGAAAAT GTACCCTG                                                                                          18

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGGACCAACA ACATC                                                                                             15

( 2 ) INFORMATION FOR SEQ ID NO:6:

( i ) SEQUENCE CHARACTERISTICS:
        ( A ) LENGTH: 780 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..780

( x i ) SEQUENCE DESCRIPTION: SEQ ID NO:6:

```
GAA  GTT  CAA  CTG  CAA  CAG  TCT  GGT  CCT  GAA  TTG  GTT  AAA  CCT  GGC  GCC        48
Glu  Val  Gln  Leu  Gln  Gln  Ser  Gly  Pro  Glu  Leu  Val  Lys  Pro  Gly  Ala
 1                    5                        10                       15

TCT  GTG  CGC  ATG  TCC  TGC  AAA  TCC  TCA  GGG  TAC  ATT  TTC  ACC  GAC  TTC        96
Ser  Val  Arg  Met  Ser  Cys  Lys  Ser  Ser  Gly  Tyr  Ile  Phe  Thr  Asp  Phe
              20                       25                       30

TAC  ATG  AAT  TGG  GTT  CGC  CAG  TCT  CAT  GGT  AAG  TCT  CTA  GAC  TAC  ATC       144
Tyr  Met  Asn  Trp  Val  Arg  Gln  Ser  His  Gly  Lys  Ser  Leu  Asp  Tyr  Ile
         35                       40                       45

GGG  TAC  ATT  TCC  CCA  TAC  TCT  GGG  GTT  ACC  GGC  TAC  AAC  CAG  AAG  TTT       192
Gly  Tyr  Ile  Ser  Pro  Tyr  Ser  Gly  Val  Thr  Gly  Tyr  Asn  Gln  Lys  Phe
    50                       55                       60

AAA  GGT  AAG  GCC  ACC  CTT  ACT  GTC  GAC  AAA  TCT  TCC  TCA  ACT  GCT  TAC       240
Lys  Gly  Lys  Ala  Thr  Leu  Thr  Val  Asp  Lys  Ser  Ser  Ser  Thr  Ala  Tyr
65                       70                       75                       80

ATG  GAG  CTG  CGT  TCT  TTG  ACC  TCT  GAG  GAC  TCC  GCG  GTA  TAC  TAT  TGC       288
Met  Glu  Leu  Arg  Ser  Leu  Thr  Ser  Glu  Asp  Ser  Ala  Val  Tyr  Tyr  Cys
                        85                       90                       95

GCC  GGC  TCC  TCT  GGT  AAC  AAA  TGG  GCC  ATG  GAT  TAT  TGG  GGT  CAT  GGT       336
Ala  Gly  Ser  Ser  Gly  Asn  Lys  Trp  Ala  Met  Asp  Tyr  Trp  Gly  His  Gly
              100                      105                      110

GCT  AGC  GTT  ACT  GTG  AGC  TCT  GGT  GGC  GGT  GGC  TCG  GGC  GGT  GGT  GGG       384
Ala  Ser  Val  Thr  Val  Ser  Ser  Gly  Gly  Gly  Gly  Ser  Gly  Gly  Gly  Gly
         115                      120                      125

TCG  GGT  GGC  GGC  GGA  TCA  GAC  ATA  GTA  CTG  ACC  CAG  TCT  CCA  GCT  TCT       432
Ser  Gly  Gly  Gly  Gly  Ser  Asp  Ile  Val  Leu  Thr  Gln  Ser  Pro  Ala  Ser
    130                      135                      140

TTG  GCT  GTG  TCT  CTA  GGA  CAA  AGG  GCC  ACG  ATA  TCC  TGC  CGA  TCC  AGC       480
Leu  Ala  Val  Ser  Leu  Gly  Gln  Arg  Ala  Thr  Ile  Ser  Cys  Arg  Ser  Ser
145                      150                      155                      160

CAA  AGT  CTC  GTA  CAT  TCT  AAT  GGT  AAT  ACT  TAT  CTG  AAC  TGG  TAC  CAA       528
Gln  Ser  Leu  Val  His  Ser  Asn  Gly  Asn  Thr  Tyr  Leu  Asn  Trp  Tyr  Gln
                        165                      170                      175

CAG  AAA  CCA  GGA  CAG  CCA  CCC  AAG  CTT  CTC  ATC  TAT  AAG  GTA  TCC  AAC       576
Gln  Lys  Pro  Gly  Gln  Pro  Pro  Lys  Leu  Leu  Ile  Tyr  Lys  Val  Ser  Asn
```

-continued

| | | | | 180 | | | | | 185 | | | | | 190 | | | |
|---|---|---|---|---|---|---|---|---|---|---|---|---|---|---|---|---|---|
| CGA | TTC | TCT | GGA | GTC | CCT | GCC | AGG | TTC | AGT | GGC | AGT | GGG | TCT | GAG | TCA | | 624 |
| Arg | Phe | Ser | Gly | Val | Pro | Ala | Arg | Phe | Ser | Gly | Ser | Gly | Ser | Glu | Ser | | |
| | | 195 | | | | | 200 | | | | | 205 | | | | | |
| GAC | TTC | ACC | CTC | ACC | ATC | GAT | CCT | GTG | GAG | GAA | GAT | GAT | GCT | GCA | ATA | | 672 |
| Asp | Phe | Thr | Leu | Thr | Ile | Asp | Pro | Val | Glu | Glu | Asp | Asp | Ala | Ala | Ile | | |
| | 210 | | | | | 215 | | | | | 220 | | | | | | |
| TAT | TAC | TGT | AGC | CAA | ACT | ACG | CAT | GTT | CCA | CCC | ACG | TTC | GGC | TCG | GGG | | 720 |
| Tyr | Tyr | Cys | Ser | Gln | Thr | Thr | His | Val | Pro | Pro | Thr | Phe | Gly | Ser | Gly | | |
| 225 | | | | | 230 | | | | | 235 | | | | | 240 | | |
| ACC | AAG | CTG | GAG | CTG | AAA | CGT | GCT | AGC | CAG | CCA | GAA | CTC | GCC | CCG | GAA | | 768 |
| Thr | Lys | Leu | Glu | Leu | Lys | Arg | Ala | Ser | Gln | Pro | Glu | Leu | Ala | Pro | Glu | | |
| | | | | 245 | | | | | 250 | | | | | 255 | | | |
| GAC | CCC | GAG | GAC | | | | | | | | | | | | | | 780 |
| Asp | Pro | Glu | Asp | | | | | | | | | | | | | | |
| | | | 260 | | | | | | | | | | | | | | |

ANTIBODY SELECTION METHODS USING CELL SURFACE EXPRESSED LIBRARIES

This application is a continuation-in-part of U.S. Ser. No. 08/258,543, filed Jun. 10, 1994, now abandoned which is a divisional of application Ser. No. 07/794,731, filed Nov. 15, 1991, now U.S. Pat. No. 5,348,867 issued Sep. 20, 1994, all of which is incorporated by reference without disclaimer.

The Government has rights in the present invention pursuant to National Science Foundation grant number BCS-9412502.

BACKGROUND OF THE INVENTION

I. Field of the Invention

The invention relates generally to antibody selection and immunoassay technology and specifically to remarkably efficient and rapid polypeptide library screening methods. The invention also includes competitive immunoassays for analyte detection. The disclosed methods open the way for production of kilogram quantities of antibodies from inexpensively maintained microorganism cultures.

II. Description of Related Art

Antibodies are of increasing importance in human therapy, assay procedures and diagnostic methods. However, methods of identifying antibodies and production of antibodies is often expensive, particularly where monoclonal antibodies are required. Hybridoma technology has traditionally been employed to produce monoclonal antibodies, but these methods are time-consuming and result in isolation and production of limited numbers of specific antibodies. Additionally, relatively small amounts of antibody are produced; consequently, hybridoma methods have not been developed for a large number of antibodies. This is unfortunate as the potential repertoire of immunoglobulins produced in an immunized animal is quite high, on the order of $>10^{10}$, yet hybridoma technology is too complicated and time consuming to adequately screen and develop large number of useful antibodies.

One approach to this problem has been the development of library screening methods for the isolation of antibodies (Huse et al, 1989; McCafferty et al, 1990; Chiswell & McCafferty, 1992; Chiswell & Clackson, 1992; Clackson, 1991). Functional antibody fragments have been produced in *E. coli* cells (Skerra & Pluckthun, 1988; Better et al, 1988; Orlandi et al, 1989; Sastry et al, 1989) as "libraries" of recombinant immunoglobulins containing both heavy and light variable domains (Huse et al, 1989). The expressed proteins have antigen-binding affinity comparable to the corresponding natural antibodies. However, it is difficult to isolate high binding populations of antibodies from such libraries and where bacterial cells are used to express specific antibodies, isolation and purification procedures are usually complex and time-consuming.

Combinatorial antibody libraries generated from phage lambda (Huse et al, 1989) typically include millions of genes of different antibodies but require complex procedures to screen the library for a selected clone. Methods have been reported for the production of human antibodies using the combinatorial library approach in filamentous bacteriophage. A major disadvantage of such methods is the need to rely on initial isolation of the antibody DNA from peripheral human blood to prepare the library. Moreover, the generation of human antibodies to toxic compounds is not feasible owing to risks involved in immunizing a human with these compounds.

Currently the most widely used approach for screening polypeptide libraries is to display polypeptides on the surface of filamentous bacteriophage (Smith, 1991; Smith, 1992). The polypeptides are expressed as fusions to the N-terminus of a coat protein. As the phage assembles, the fusion proteins are incorporated in the viral coat so that the polypeptides become displayed on the bacteriophage surface. Each polypeptide produced is displayed on the surface of one or more of the bacteriophage particles and subsequently tested for specific ligand interactions. While this approach appears attractive, there are numerous problems, including difficulties of enriching positive clones from phage libraries. Enrichment procedures are based on selective binding and elution onto a solid surface such as an immobilized receptor. Unfortunately, avidity effects arise due to multivalent binding of the phage and the general tendency of phage to contain two or more copies of the displayed polypeptide. The binding to the receptor surface therefore does not depend solely on the strength of interaction between the receptor and the displayed polypeptide. This causes difficulties in the identification of clones with high affinity for the receptor; thus, there remain distinct deficiencies in the methods used to isolate and screen polypeptides, particularly antibodies, even in view of the development of phage libraries.

Moreover, there is a significant need for procedures that are rapid and inexpensive relative to cost of currently used techniques.

Immunoassays have typically been used for the detection of antigens or antibodies, less frequently for determination of other classes of compounds. Immunoassays can be generally divided into two types: heterogeneous assays requiring multiple separation steps, and homogeneous assays which are performed directly. Heterogeneous immunoassays in general involve a ligand or antibody immobilized on a solid matrix. A sample containing an analyte is contacted with the immobilized antibody and the amount of complex formed on the matrix support is determined from a label attached directly or indirectly to the immobilized complex.

Heterogeneous immunoassays may be performed as sandwich assays in which a molecule of interest is reacted with an immobilized antibody that specifically binds that molecule with high affinity. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of analyte in the sample, is measured.

ELISA or enzyme-linked immunosorbent assay is one example of an immunoassay. ELISAs are extensively used in biotechnology applications, particularly as immunoassays for a wide range of antigenic substances. The sensitivity of ELISA is based on the enzymatic amplification of the signal.

However, despite such widespread use, ELISA has several disadvantages, including inconvenience and expense that preclude more general use. Additionally, immunoassays depend on the availability of antibodies, which is frequently a major consideration in terms of cost or feasibility of a specific assay. Several washing steps may often be required in ELISA procedures to remove excess antibody not bound to the immobilization support or to remove excess analyte or antibody following the primary binding reaction. The steps necessary to remove excess enzyme-conjugate that does not bind to the immobilized antibody-analyte complex may significantly increase assay time and cost.

There has been some effort to provide semi-automation of ELISA, for example the apparatus and method described in U.S. Pat. No. 4,981,785. However, these methods involve not only the expense of the equipment and training of specialized personnel, but also fail to provide rapid and economical quantitation of analytes.

Unfortunately, alternative analytical methods for quantitative determination of trace amounts of many analytes, including not only polypeptides but also organic species such as toxic chemicals, typically involve relatively complex and inconvenient procedures. In most cases, samples must be collected, extracted and prepared for specific analyses. Procedures frequently involve use of hazardous chemicals such as organic solvents and/or radioactive material, thereby adding to cost.

Recent advances in biotechnology, specifically the advent of monoclonal antibodies and the use of enzyme labels in place of radiolabels, have promoted a rapid expansion of immunoassay applications to include the detection of certain toxic chemicals (Collins, 1985; Gould and Marx, 1988; Stanker, 1989; Watkins, 1989; Roberts, 1989). Enzyme labels, for example, are particularly useful because the catalytic properties of the enzyme provide powerful biochemical amplification, thereby allowing detection of extremely low analyte concentrations. However, the utility of this type of detection may be limited if the binding site of the antibody is not available or the sample solution contains interfering substances.

Enzyme-amplified immunoassay techniques have been applied to the determination of different drug species. In this system a hapten-enzyme conjugate is prepared so that enzyme activity is retained after conjugation. When the conjugate binds with the hapten-specific antibody there is a loss in enzyme activity. Any free hapten (drug) in a sample reduces the inhibition by competing for antibody binding sites. Enzyme activity is thus proportional to concentration of free hapten. This type of assay has been developed by the Syva Company (Palo Alto, Calif.) under the trademark EMIT. However, the EMIT assay is less satisfactory for detection of relatively large molecules such as proteins.

Immunodetection technology employing solid phase enzyme immunoassay for detection of certain environmental waste by-products has been reported (Huber, 1985). For example, the agricultural chemical Atrazine was reported detectable in the 1.1 to 2200 ppb range. Enzyme immunoassay (EIA) sensitivity was further improved by using spheres as antibody carriers and by using affinity purified antibodies. While this is a step forward in the ability to detect low levels of environmental contaminants, the procedures are time-consuming and costly.

Immunoassays represent a powerful technique for the identification and quantification of specific molecules. Radio Immunoassay (RIA) and ELISA techniques currently form the basis of many medical diagnostic procedures. However, solid phase immunoassays rely on isolated and purified antibodies that may be prohibitively expensive. In cases where the detection reagent is an enzyme or radiolabeled material, additional considerations are safety, equipment and technical manpower cost.

Despite some progress and ongoing efforts to expand the availability and identification of useful antibodies for immunoassays, there is a lack of rapid and inexpensive antibody screening methods. Available technologies have failed to provide means to cost effectively produce large quantities of such antibodies. Additionally, despite the wide application of immunoassay methods, most are complex, often slow and frequently employ hazardous reagents.

SUMMARY OF THE INVENTION

The present invention addresses these and other drawbacks inherent in the prior art by providing new methods of antibody selection and production. For the first time it is possible to rapidly screen polypeptide libraries for potential antibodies; often in a matter of hours. The disclosed methods allow production of large quantities of antibodies, potentially on a kilogram scale, from microorganism cultures. And, because selected antibodies can be displayed on the surface of a host cell, immunoassays can be conducted with remarkable rapidity.

In one aspect of the invention, expression libraries are prepared such that an expressed protein is displayed on the surface of a cell. Typically the polypeptides will be surface expressed in a host cell such as bacterial, yeast, insect, eukaryotic or mammalian cells. Gram negative bacterial cells are preferred, particularly E. coli, although Salmonella, Klebsiella, Erwinia, Pseudomonas aeruginosa, Haemophilus influenza, Rickettsia rickettsii, Neisseria gonorrhea, etc are also expected to be suitable. While examples have utilized a bacterial host cell for surface expression, it is contemplated that other microorganisms may prove useful; for example, yeasts, molds, algae, eukaryotes, as well as other prokaryotes and single cell microorganisms.

Surface expression of a polypeptide, e.g. antibody, on a cell surface is achieved using a recombinant vector that promotes display on the outer membrane of a host cell. Vectors are such as those of the general construction described in U.S. Pat. No. 5,348,867, incorporated herein by reference. Generally the vectors will be appropriate for a bacterial host cell and will include at least three DNA segments as part of a chimeric gene. One segment is a DNA sequence encoding a polypeptide that targets and anchors a fusion polypeptide to a host cell outer membrane. A second DNA segment encodes a membrane-transversing amino acid sequence, i.e. a polypeptide that transports a heterologous or homologous polypeptide through the host cell outer membrane. The third DNA segment encodes any of a number of desired polypeptides.

Such vectors will display fusion polypeptides at the exterior of a host cell. These recombinant vectors include a functional promoter sequence.

Expression of recombinant proteins such as antibodies or antibody fragments on the cell surface of gram-negative bacteria is achieved by fusion to segments of a major lipoprotein and OmpA; however, fusion to protein domains other than those derived from the major lipoprotein and OmpA is also envisioned, provided that these domains can function for the expression of the desired polypeptide on the cell surface. Generally, the desired antibody, antibody fragment or peptide is fused to an amino acid sequence that includes the signals for localization to the outer membrane and for translocation across the outer membrane. The amino acid sequences responsible for localization and for translocation across the outer membrane may be derived either from the same bacterial protein or from different proteins of the same or different bacterial species. Examples of proteins that may serve as sources of localization signal domains are shown in Table 2.

TABLE 2

EXAMPLES OF OUTER MEMBRANE TARGETING SEQUENCES

| | Organism |
|---|---|
| Lpp | E. coli (or functional equivalent in Salmonella) |
| TraT | E. Coli (or functional equivalent in Salmonella) |

TABLE 2-continued

EXAMPLES OF OUTER MEMBRANE TARGETING SEQUENCES

| | Organism |
|---|---|
| OsmB | E. coli (or functional equivalent in Salmonella) |
| N1pB | E. coli (or functional equivalent in Salmonella) |
| BlaZ | E. coli (or functional equivalent in Salmonella) |
| Lpp1 | Pseudomonas aeruginosa |
| PA1 | Haemophilus influenza |
| OprI | |
| 17 kDa lpp | Riokettsia riokettsii |
| H.8 protein | Neisseria gonorrhea |

In addition a sequence that allows display of the polypeptide on the cell surface is required. Appropriate examples are shown in Table 3.

TABLE 3

EXAMPLES OF TRANSMEMBRANE SEQUENCES

| OmpA | E. coli or functional equivalent in Salmonella |
|---|---|
| LamB | E. coli or functional equivalent in Salmonella |
| PhoE | E. coli or functional equivalent in Salmonella |
| OmpC | E. coli or functional equivalent in Salmonella |
| OmpF | E. coli or functional equivalent in Salmonella |
| OmpT | E. coli or functional equivalent in Salmonella |
| FepA | E. coli or functional equivalent in Salmonella |

Of course similar considerations also apply to host cells other than bacteria, including eukaryotic, yeast, molds, etc. as previously discussed.

Screening for antibodies employing the methods of the present invention allows one to select an antibody or antibody fragment from a plurality of candidate antibodies that have been expressed on the surface of a host cell. In most instances the host cell will be a bacterial cell, preferably E. coli. The antibodies are obtained from an expression vector library that may be prepared from DNAs encoding antibodies or antibody fragments. One source of such DNAs could be from an animal immunized with a selected antigen; alternatively, antibody genes from other sources can be used, such as those produced by hybridomas or produced by mutagenesis of a known antibody gene. One preferred method of obtaining DNA segments is to isolate mRNA from antibody cells of an immunized animal. The mRNA may be amplified, for example by PCR, and used to prepare DNA segments to include in the vectors. One may also employ DNA segments that have been mutagenized from one or more DNAs that encode a selected antibody or antibody fragment.

Once an antibody expression library is prepared, the selected antigen for which one desires to identify and isolate specific antibody or antibodies is labeled with a detectable label. There are many types of detectable labels, including fluorescent labels, the latter being preferred in that they are easily handled, inexpensive and nontoxic. The labeled antigen is contacted with the cells displaying the antibody expression library under conditions that allow specific antigen-antibody binding. Conditions can be varied so that only very tightly binding interactions occur; for example, by using very low concentrations of labeled antigen.

Identifying the antibody or antibody fragment expressing cells may be accomplished by methods that depend on detecting the presence of the bound detectable label. A particularly preferred method for identification and isolation is cell sorting or flow cytometry. On aspect of this method is fluorescence activated cell sorting (FACS).

Identification of antibody expressing bacteria by FACS is directly based on the affinity for the soluble hapten thus eliminating artifacts due to binding on solid surfaces. This means only the high affinity antibodies are recovered by sorting following binding of low concentrations of fluorescently labeled antigen. There is no analogous method for specifically selecting phage with very high affinity. Additionally, the sorting of positive clones is essentially quantitative. It is limited only by the accuracy of the flow cytometer which is on the order of 95%. In contrast with phage technology, the efficiency of selection is not limited by avidity effects because screening does not depend on binding to a surface having multiple attachment sites.

Following selection of high affinity clones, the production of soluble antibodies can be achieved easily without the need for further subcloning steps. Thus, the clones may be maintained under standard culture conditions and employed to produce the selected antibody. Production of antibody is limited only to the scaleup of the cultures.

The invention further includes competitive binding assays using cells with antibodies or analyte-combining antibody fragments expressed on the outer cell surface.

As used in the context of the present invention, analyte is defined as a species that interacts with a non-identical molecule to form a tightly bound, stable complex. For practical purposes, the binding affinity is usually greater than about $10^6 M^{-1}$ and is preferably in the range of $10^9–10^{15} M^{-1}$. The analyte may be any of several types of organic molecules, including alicyclic hydrocarbons, polynuclear aromatics, halogenated compounds, benzenoids, polynuclear hydrocarbons, nitrogen heterocyclics, sulfur heterocyclics, oxygen heterocyclics, and alkane, alkene alkyne hydrocarbons, etc. Biological molecules are of particular interest, including amino acids, peptides, proteins, lipids, saccharides, nucleic acids and combinations thereof. Of course it will be understood that these are by way of example only and that the disclosed immunoassay methods are applicable to detecting an extraordinarily wide range of compounds, so long as one can obtain an antibody that binds with the analyte of interest.

The disclosed whole cell immunoassay methods allow rapid detection of a wide range of analytes and are particularly useful for determination of polypeptides. The methods have been developed to take advantage of the binding characteristics of bacterial cell surface exposed anti-analyte antibodies. Such surface displayed antibodies are stable and bind readily with specific analytes. This unique form of protein expression and immobilization thus has provided the basis of an extremely rapid competitive assay that may be performed in a single reaction vessel in an "add and measure" format. Such assays can be described as "one-pot" reactions that make possible in situ detection of an analyte.

A particular advantage of cell surface expressed antigen-binding antibodies is that the antibody is attached to the outer membrane of the cell. The cells therefore act as a solid support during the assay, thereby eliminating many of the manipulations typically required in preparing reagents required for existing immunoassay techniques. Optionally, cells with the antibody displayed on the surface may themselves be attached to a solid support such as a membrane, dipstick or beads to further facilitate removal of the cells following the assay.

The immunoassays of the present invention may be used to quantitate a wide range of analytes. Generally, one first obtains the appropriate host cell culture where the antianalyte antibody is displayed on the host cell surface, calibrates with standard samples of analyte, then runs the assay with a measured volume of unknown concentration of analyte.

In conducting a competitive immunoassay in accordance with the disclosed methods, one first obtains a gram negative host cell that expresses an analyte binding antibody. The host cell is then contacted with a standard analyte sample that contains a known amount of an analyte linked to a detectable label employing conditions effective for forming an immune complex. Once calibration is completed, the same procedure is used with a second host cell that has the same antibody or analyte-combining fragment expressed on its surface, except that in addition to the standard labeled analyte sample, a test sample in which an unknown amount of analyte is to be determined is added. One is not limited to using the same host cell in this procedure.

In the actual assay, a known amount of the antibody-covered cells are placed in a solution of a known concentration of the analyte-conjugate along with an unknown concentration of the analyte (the test solution). The analyte conjugate competes with free analyte in solution for binding to the antibody molecules on the cell surface. The higher the concentration of analyte conjugate in the solution, the fewer molecules of fluorescein analyte conjugate bind on the surface of the cells, and vice versa.

The mixture is centrifuged to pellet the cells, and the fluorescence of the supernatant is measured. The assay is quantitative because the amount of observed fluorescence is proportional to the concentration of analyte in the test sample, i.e., if there is a very low concentration of analyte to compete with the fluorescein conjugate, then most of the conjugate will bind to the cells and will be removed from solution. The more molecules of analyte in solution, the more molecules of analyte bind to the antibodies thereby preventing the conjugate from binding. In this case, more fluorescein conjugate remains in the supernatant to give a stronger fluorescence signal. The assay can be calibrated to generate a quantitative measurement of the unknown concentration of analyte. The entire assay requires less than one hour. Fluorescence determinations may be made with a basic fluorimeter.

Gram negative host cells are preferred in the practice of the invention. Generally one will wish to use *E. coli* or Salmonella and to surface-express an analyte-binding antibody suitable for determination of a selected antigen. Methods for surface-expression of a wide range of polypeptides are found in U.S. Pat. No. 5,348,867, incorporated herein in its entirety by reference. Virtually any antibody may be surface expressed in this manner, including antibodies fused to polypeptides, catalytic antibodies and multi-antibody fusions.

As used herein, the term "contacting" is defined as bringing the reaction components into close enough proximity to each other to allow the desired reaction to occur. Contacting may be by mixing the components in solution, for example, or by heterogeneous interaction such as by flow contact through a column or immobilizing matrix that binds to one of the components.

In preferred embodiments the immunoassay is performed to quantitate the amount of analyte in a sample. Cells surface-expressing an analyte-combining antibody are preferably incubated with limiting concentrations of an analyte, preferably labeled. Any of a wide variety of labels may be employed; however, fluorescence labels are particularly preferred for the several advantages over other labels. For example, enzyme labels may not be accurate if enzyme activity is compromised, such as from solution contaminants; radiolabels are not only expensive but also pose a hazard. Safety precautions are usually required by law and may be quite stringent. In contrast, fluorescence labels are relatively inexpensive and, more significantly in terms of cost, can be detected using only a basic fluorimeter rather than more complicated and costly instrument.

The competitive immunoassay discussed above requires one to set up a control sample. This sample comprises a second host cell expressing an analyte binding antibody. This is contacted with a known amount of analyte linked to a detectable label and a known amount of unlabeled analyte, i.e. the analyte to be detected or determined in the assay. After formation of the immunocomplexes, one measures the free label in solution after the cells have been separated. This measures the amount of residual detectable label as the decrease in, e.g., fluorescence emission, from which the amount of unknown analyte may be determined. A preferred fluorescent label is fluorescein. The inventors have found that measurement of the amount of residual label that is not bound to antibodies is proportional to the amount of analyte label in solution. This provides the basis for quantitative measure in that the increase in the amount of label is directly proportional to the analyte. Alternatively, the label may be measured in the complexes. In this type of measurement, the analyte is inversely proportional to the amount of label.

Of course fluorescence labeling, while preferred, does not preclude the use of other detectable agents such as chemiluminescent agents, electrochemiluminescent agents, radioactive labels, enzymatic labels that form a colored product with a chromogenic substrate as well as other fluorescent compounds. A preferred fluorescent label is fluorescein while $Ru(bpy)_3^{2+}$ is preferred for use as an electrochemiluminescent agent.

The invention is readily adaptable to the determination of multiple analytes. This is achieved using two or more different analyte-binding antibodies expressed in separate host cells. It is also possible to surface express more than one antibody on the surface of a particular host cell; however, this may cause interference in binding. One will, in these situations, use different detecting agents; for example, two different fluorescent labels, each with distinct emissions, such as fluorescein which emits at 520 nm and Texas Red which emits at 620 nm.

Also included as part of the invention are expression vector libraries. Such libraries include cells that surface display a plurality of antibodies or antibody fragments. Gram negative cells are preferred, particularly *E. coli*. The antibody or antibody fragments will have distinct antigen-combining regions or metal binding sites. The surface-displayed antibodies may be catalytic antibodies or antibody conjugates such as fusion proteins that include reporter molecules, e.g. alkaline phosphatase, luciferase, β-lactamase, etc.

In certain aspects of the invention, host cells displaying an antibody or antibodies on the surface may be used to stimulate an immune response. Such responses will be obtained by administering to an animal a pharmaceutical composition that includes an immunologically effective amount of a host cell, preferably Gram negative and more preferably E. coli, that expresses an antibody or antigen-combining antibody fragment on its outer membrane surface.

As part of the invention, immunoassay kits are also envisioned comprising a container having suitably aliquoted reagents for performing the foregoing methods. For example, the containers may include one or more bacterial cells with particular surface expressed analyte-binding antibodies. Suitable containers might be vials made of plastic or glass, various tubes such as test tubes, metal cylinders, ceramic cups or the like. Containers may be prepared with a wide range of suitable aliquots, depending on applications and on the scale of the preparation. Generally, this will be an amount in conveniently handled form, such as freeze-dried preparations, and sufficient to allow rapid growth of the bacterial cells as required.

Such kits may optionally include surface-expressed antibodies in host cells that are immobilized on surfaces appropriate for the intended use. One may for example, provide the cells attached to the surface of microtiter plates, adsorbent resins, cellulose (e.g. filter paper), polymers, glass beads, etc.

For certain applications a kit containing a population of viable gram negative host cells that express a distinct analyte-binding antibody and also including a sample of analyte linked to a detectable label is envisioned. Analyte standards of the analyte may be included.

The disclosed methods offer numerous advantages over current practice, not the least of which is the adaptation to production of large quantities of antibodies. The convenience, safety and low-cost of bacterial cultures are important in commercial considerations. The screening and assay methods are rapid, simple and may be set up with relatively low capitalization cost as the equipment required is low-maintenance and does not require highly technically trained personnel to operate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A and FIG. 1B. Nucleotide and amino acid sequence of the anti-digoxin single chain $F_v$ antibody fragment.

FIG. 4A. JM109/pTX152 sample used as a negative control.

FIG. 4B. JM109/pTX152 sample used as a positive control.

FIG. 4C. JM109/pTX152 pretreated with 0.2 mg/ml trypsin.

FIG. 4D. JM109/pTX152 pretreated with free digoxin.

FIG. 4E. A 100,000:1 mixture of JM109/pTX101:JM109/pTX152 prior to the first cell sorting run.

FIG. 4F. A 100,000:1 mixture after growing cells recovered from the first cell sorting run.

FIG. 4G. A 100,000:1 mixture after growing cells recovered from the second cell sorting run.

FIG. 5. The sequences of the primers used for the PCR amplification of mRNA isolated from spleen cells for the construction of single chain antibody libraries from immunized animals.

DETAILED DESCRIPTION OF PREFERRED EMBODIMENTS

Antibody Screening Methods

Figure 2A:
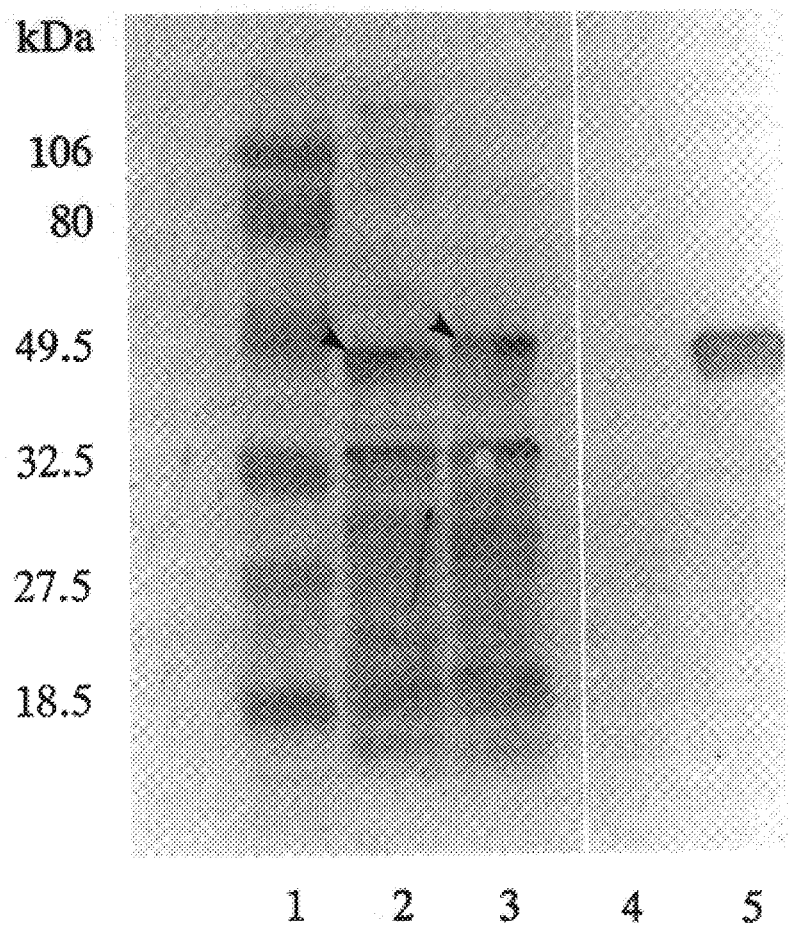
FIG. 2A. Western blot analysis of total membrane fractions from E. coli JM109 cells containing pTX101 (Lanes 2 and 4); JM109/pTX152 (Lanes 3 and 5) and probed with anti-OmpA antibodies at 1:5000 dilution; Lanes 4 and 5 were probed with monoclonal anti-HSV antibodies at 1:5000 dilution. Arrowheads indicate the Lpp-OmpA-β-lactamase fusion (lane 2) and the Lpp-OmpA-scFv(digoxin) fusion (lane 3). The 32 kDa band in lanes 2 and 3 corresponds to OmpA. Lane 1, molecular mass markers (in kDa).

The development of methods that allow cell surface display of virtually any polypeptide on the surface of a host cell, and particularly to achieve stable anchoring and polypeptide display on the surface of a bacterial cell such as E. coli, has provided the basis for new methods of rapid and efficient selection of antibodies from antibody libraries expressed in the host cells. Likewise, bacterial surface-displayed peptide libraries may be analogously employed to identify new antigens or epitopes to an antibody.

The novel methods herein disclosed are particularly advantageous because they allow unprecedented rapid and efficient selection, purification and screening of polypeptide libraries from bacterial host cell surfaces, providing several advantages over phage libraries. Unlike most other methods used for screening and assay, the disclosed methods are well-suited for commercial adaptation.

Expense is a major consideration in commercial production. The methods herein disclosed employ bacterial cells such as E. coli. These cells are inexpensive to produce and are convenient to work with. Kilogram quantities of cells can be produced overnight for a few dollars worth of media. Antibodies used in current immunoassays may cost $100/gm or more to produce; total costs are even higher once purification and personnel costs are factored in.

Assay procedures are greatly facilitated because antibodies are displayed on the surface of cells. This permits use of simple centrifugation to remove the cells from an assay sample. Assays are thus very rapid, and inexpensive because centrifugation does not require complex or expensive equipment.

Bacterial cells in which antibodies have been expressed may be readily immobilized, thus allowing rapid recovery and efficient removal from the system. One may use membranes, dipsticks or beads through a chemically promoted coupling reaction in addition to other well-known immobilization matrices. In this manner, the cells can be separated from the solution without the need for a centrifugation step.

Bacterial cultures may be supplied in forms that have an indefinite shelf life and yet can be readily prepared for use; for example as "stab cultures" or lyophilized preparations; the user may prepare large amounts in liquid culture as needed. The reagent is thus renewable as compared with the current antibody reagents that are "used up" and must be continually replaced. Bacterial cultures may be prepared fresh without concern about shelf-life of reagents that must be stored until use.

Many current immunoassays use radioactive agents or relatively complex equipment, e.g., polarizing fluorimeters. The disclosed assay methods require relatively inexpensive cell culturing equipment, a clinical centrifuge, and in one aspect of the assay, a fluorimeter. Daily assay costs are negligible, without concerns about radioactivity or other toxic materials, or expensive maintenance contracts and downtime that are frequent concerns in using complex equipment.

The screening methods are practiced by first constructing an antibody library using any of several well-known techniques for library construction. For example, after selecting an immunogen, one may immunize a mammal by conventional means and collect antiserum. mRNA from spleen may be used as template for PCR amplification; for example employing primers complementary to constant and variable domain framework regions of different antibody subclasses. Alternatively DNA from polyclonal populations of antibodies may be amplified, fragmented if desired, ligated into pTX101 or a similar vector as described in U.S. Pat. No. 5,348,867, incorporated herein by reference, and transformed into an *E. coli* cell. The DNA may be introduced by electroporation, gene gun, etc.

*E. coli* surface displayed antibodies may be rapidly and efficiently sorted using fluorescence activated cell sorting techniques (FACS).

Immunoassay Methods

For the first time, a competitive immunoassay has been developed that takes advantage of anti-analyte binding antibodies immobilized on a bacterial cell surface. Several advantages of the disclosed immunoassay include generally the convenience, wide applicability and the simplicity, rapidity and sensitivity of the assay.

The present invention involves a novel method of carrying out competitive immunoassays using antibodies attached to the surface of cells. The disclosed immunoassays are useful for binding, purifying, removing, quantifying or otherwise generally detecting analytes. Antibodies expressed on bacterial cell surfaces have been shown surprisingly adaptable for use in competitive immunoassay procedures.

The immunoassay methods are carried out using antibodies attached to the surface of cells. One selects an antibody known to bind tightly and specifically to a molecule to be detected, or what is referred to herein as the analyte. The analyte may be a medically relevant molecule, a marker molecule used in reactions, a pesticide or a toxic species of interest. In order to conduct the assay, a sample of the analyte is labeled, typically with a fluorescent moiety such as fluorescein. Fluorescein may be covalently bound to an analyte such as a protein using methods well known to the synthetic chemist. A covalent conjugate with the analyte is formed.

In a particular example, the analyte digoxin, a cardiac glycoside, was determined using fluorescein-digoxin conjugate. The assay was quantitative with a sensitivity in the nanomolar range.

The invention also provides methods of removing undesirable components from a given sample, as exemplified by removing viral or other contaminants from blood samples, removing environmental contaminants from water samples, and the like. The cells expressing the antibody fragment on their surface are contacted with the sample, allowed to react and the cells removed by simple centrifugation to obtain a purified sample.

Cells expressing an antibody fragment on their surface may also be linked to a solid support, such as in the form of beads, membrane or a column matrix, and the sample suspected of containing the unwanted antigenic component applied to the immobilized antibody. A purged or purified sample is then obtained free from the unwanted antigen simply by collecting the sample from the column and leaving the antigen immunocomplexed to the immobilized antibody.

Detection of immunocomplex formation is well known in the art and may be achieved through the application of numerous approaches. These approaches are typically based upon the detection of a label or marker, such as any of the radioactive, fluorescent, chemiluminescent, electrochemiluminescent, biological or enzymatic tags or labels known in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The first added component that becomes bound within the primary immune complexes may be detected by means of a second binding ligand that has binding affinity for the surface expressed antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining label in the secondary immune complexes is then detected.

Further methods include the detection of primary immune complexes by a two step approach. A second binding ligand, such as an antibody, that has binding affinity for the surface expressed antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunoassay methods of the present invention have evident utility in the diagnosis of certain medical conditions such as pregnancy where detection of a specific analyte is diagnostic of a medical condition. Here, a biological or clinical sample suspected of containing a specific analyte is contacted with the surface expressed antibody and detected according to any of the methods outline above. However, these embodiments also have applications to non-clinical samples, such as in the titering of analyte or antibody samples, and in the selection of hybridomas.

In certain uses of the assay, cells containing antibodies on the surface are produced as described previously. Antibodies known to bind tightly and specifically to a molecule of interest are employed. The molecule could be a medically relevant molecule, a marker molecule used in a scientific study, a pesticide of environmental concern in groundwater, etc. A covalent conjugate of the molecule with a fluorescent moiety such as fluorescein is synthesized for use as a probe in binding. Other detection agents include radioactive compounds, enzyme conjugates, chemiluminescent reagents such as luciferase and electrochemiluminescent reagents such as $Ru(bpy)_3^{2+}$. (Yang et al., 1994; Blackburn et al., 1991). The assay may also be carried out using tritium as the labeling agent for the antigen and performing a radioimmunoassay. The radioactivity may be detected using a scintillation counter to measure binding constants up to $10^{-8}$ or $10^{-9}M^{-1}$.

To perform the preferred assay, a known amount of the antibody-covered cells are placed in a solution of a known concentration of the molecule-fluorescein conjugate along with an unknown concentration of the molecule. The molecule-fluorescein conjugate competes with free molecules in solution for binding to the antibody on the cell surface. The higher the concentration of the molecule in the solution, the fewer molecules of fluorescein-molecule conjugate will bind to the surface of the cells, while lower concentrations of the molecule will result in more of the conjugate bound to the cell surface.

Before measuring residual fluorescence, the cells are removed from the solution, most conveniently by pelleting, and the fluorescence of the supernatant measured. The assay is quantitative because the amount of observed fluorescence is proportional to the concentration of the molecule in the unknown sample. If there is a very low concentration of the molecule to compete with the fluorescein conjugate, most of the conjugate will bind to the cells and will be removed from the solution. The higher the concentration of the molecule in solution, the more molecules bind to the antibodies thereby preventing the conjugate from binding. In this case, more fluorescein conjugate remains in the supernatant to give a stronger fluorescent signal. The assay can be calibrated to generate a quantitative measurement of the unknown concentration of the molecule. The entire assay takes less than an hour and requires only a basic fluorimeter.

The cells with the antibody fragment displayed on their surface may be attached to a solid support such as a membrane, dipstick or beads to facilitate the removal of the antibody following reaction with antigen.

Expression Library Selection Methods
Vector Constructs

The present invention involves the display of antibody molecules on the surface of a bacteria. As used herein, the term "antibody" or "antibody fragment" is used to refer to any immunologic binding agent such as IgG, IgM, IgA, IgD and IgE or any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art.

Genes for recombinant antibodies or antibody fragments are first fused to the 3' of a sequence that encodes a cell surface targeting domain. The cell envelope of *E. coli* and other gram-negative bacteria consists of the inner membrane (cytoplasmic membrane), the peptidoglycan cell wall and the outer membrane. Although the latter normally serves as a barrier to protein secretion, a targeting sequence has been developed that, when fused to normally soluble proteins, can direct them to the cell surface (Francisco et al., 1992; 1993). The surface targeting domain includes the first nine amino acids of Lpp, the major lipoprotein of *E. coli* fused to amino acid 46–159 of the Outer Membrane Protein A (OmpA). The function of the former is to direct the chimera to the outer membrane whereas the OmpA sequence mediates the display of proteins at the C-terminal of OmpA. Lpp-OmpA (46–159) fusions have been used to anchor a variety of proteins such as β-lactamase, a cellulose binding protein and alkaline phosphatase on the *E. coli* surface. However, other analogous surface targeting domains may be employed to stably anchor the recombinant polypeptides on the cell surface.

Methods for the display of virtually any polypeptide on the surface *E. coli* are described in U.S. Pat. No. 5,348,867 issued Sep. 20, 1994, hereby incorporated by reference. Any library encoding a set of related polypeptide sequences may be displayed on the surface of *E. coli*. Examples of such libraries include, libraries derived by mutagenesis of a homologous or heterologous protein, random peptide libraries, epitope libraries and libraries of recombinant antibody fragments, all of which may be created by methods known to those skilled in the art.

Exemplary of the surface expression method is an Lpp-OmpA(46–159)-antibody fusion expressed in a gram-negative bacterium. Due to the presence of the Lpp-OmpA (46–159) sequence, the fusion is localized on the outer membrane such that the N-terminal domain is embedded in the bilayer and the antibody sequence is fully exposed on the cell surface. Recombinant antibodies expressed on the cell surface as Lpp-OmpA(46–159) fusions are functional and bind to antigens with high affinity.

Antibody Fragment Constructs

The specificity of an antibody is determined by the complementarity determining regions (CDRs) within the light chain variable regions ($V_L$) and heavy chain variable regions ($V_H$). The $F_{ab}$ fragment of an antibody, which is about one-third the size of a complete antibody contains the heavy and light chain variable regions, the complete light chain constant region and a portion of the heavy chain constant region. $F_{ab}$ molecules are stable and associate well due to the contribution of the constant region sequences. However, the yield of functional $F_{ab}$ expressed in bacterial systems is lower than that of the smaller $F_v$ fragment which contains only the variable regions of the heavy and light chains. The $F_v$ fragment is the smallest portion of an antibody that still retains a functional antigen binding site. The $F_v$ fragment has the same binding properties as the $F_{ab}$, however without the stability conferred by the constant regions, the two chains of the $F_v$ can dissociate relatively easily in dilute conditions.

To overcome this problem, $V_H$ and $V_L$ regions may be fused via a polypeptide linker (Huston et al., 1991) to stabilize the antigen binding site. This single polypeptide $F_v$ fragment is known as a single chain antibody (scF$_v$). The $V_H$ and $V_L$ can be arranged with either domain first. The linker joins the carboxy terminus of the first chain to the amino terminus of the second chain.

While the present invention has been illustrated with display of single chain $F_v$ molecules on the surface of the bacteria, one of skill in the art will recognize that heavy or light chain $F_v$ or $F_{ab}$ fragments may also be used with this system. A heavy or light chain can be displayed on the surface followed by the addition of the complementary chain to the solution. The two chains are then allowed to combine on the surface of the bacteria to form a functional antibody fragment. Addition of random non-specific light or heavy chain sequences allows for the production of a combinatorial system to generate a library of diverse members.

Antibody Fragment Gene Isolation

To accomplish construction of antibody fragments the encoding genes are isolated and then modified to permit cloning into the expression vector. Although methods can be used such as probing the DNA for $V_H$ and $V_L$ from hybridoma cDNA (Maniatis et al., 1982) or constructing a synthetic gene for $V_H$ and $V_L$ (Barbas et al., 1992), a convenient, mode is to use template directed methods to amplify the antibody sequences. A diverse population of antibody genes can be amplified from a template sample by designing primers to the conserved sequences at the 3' and 5' ends of the variable region known as the framework or to the constant regions of the antibody (Iverson et al., 1989). Within the primers, restriction sites can be placed to facilitate cloning into an expression vector. By directing the primers to these conserved regions, the diversity of the antibody population is maintained to allow for the construction of diverse libraries. The specific species and class of antibody can be defined by the selection of the primer sequences as illustrated by the large number of sequences for all types of antibodies given in Kabat et al., 1987, hereby incorporated by reference.

Messenger RNA isolated from the spleen or peripheral blood of an animal can be used as the template for the amplification of an antibody library. In certain circumstances, where it is desirable to display a homogeneous population of antibody fragments on the cell surface, mRNA may be isolated from a population of monoclonal antibodies. Messenger RNA from either source can be prepared by standard methods and used directly or for the preparation of a cDNA template.

Generation of mRNA for cloning antibody purposes is readily accomplished by following the well-known procedures for preparation and characterization of antibodies (see, e.g., Antibodies: A Laboratory Manual, 1988; incorporated herein by reference).

Generation of monoclonal antibodies (MAbs) follows generally the same procedures as those for preparing polyclonal antibodies. Briefly, a polyclonal antibody is prepared by immunizing an animal with an immunogenic composition in accordance and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, rabbits are usually preferred for production of polyclonal antibodies.

Immunogenic compositions often vary in immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Recognized means for conjugating a polypeptide to a carrier protein are well known and include glutaraldehyde, m-maleimidobenzoyl-N-hydroxysuccinimide ester, carbodiimides and bis-diazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated, stored and the spleen harvested for the isolation of mRNA from the polyclonal response or the animal can be used to generate MAbs for the isolation of mRNA from a homogeneous antibody population.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g. a small molecule hapten conjugated to a carrier, a purified or partially purified protein, polypeptide or peptide. The immunizing composition is administered in a manner effective to stimulate antibody producing cells. Rodents such as mice and rats are frequently used animals; however, the use of rabbit, sheep frog cells is also possible. The use of rats may provide certain advantages (Goding, pp. 60–61, 1986), but mice are preferred, particularly the BALB/c mouse as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from blood samples. Spleen cells and blood cells are preferable, the former because they are a rich source of antibody-producing cells that are in the dividing plasmablast stage, and the latter because blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al., 1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Simple and rapid assays include radioimmunoassays, enzyme immunoassays, cytotoxicity assays, plaque assays, dot immunobinding assays, and the like.

The selected hybridomas are serially diluted and cloned into individual antibody-producing cell lines from which clones can then be propagated indefinitely to provide MAbs.

The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Following the isolation and characterization of the desired monoclonal antibody, the mRNA can be isolated using techniques well known in the art and used as a template for amplification of the target sequence.

Amplification of Antibody Gene Fragments

A number of template dependent processes are available to amplify the target sequences present in a given template sample. One of the best known amplification methods is the polymerase chain reaction (referred to as PCR) which is described in detail in U.S. Pats. Nos. 4,683,195, 4,683,202 and 4,800,159, and in Innis et al. (1990), each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of target amplified. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as an amplification method. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having a 3' and 5' sequences of non-specific DNA and middle sequence of specific RNA is hybridized to DNA which is present in a sample. Upon hybridization, the reaction is treated with RNaseH, and the products of the probe identified as distinctive products which are released after digestion. The original template is annealed to another cycling probe and the reaction is repeated.

Other amplification methods are described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR (Kwoh et al., 1989). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; O'Hara et al., 1989).

Methods based on ligation of two (or more) oligonucleotides in the presence of nucleic acid having the sequence of the resulting "di-oligonucleotide", thereby amplifying the di-oligonucleotide, may also be used in the amplification step (Wu et al., 1989).

Amplification products may be analyzed by agarose, agarose-acrylamide or polyacrylamide gel electrophoresis using standard methods (see, e.g., Maniatis et al. 1982). For example, one may use a 1% agarose gel stained with ethidium bromide and visualized under UV light. Alternatively, the amplification products may be integrally labeled with radio- or fluorometrically-labeled nucleotides. Gels can then be exposed to x-ray film or visualized under the appropriate stimulating spectra, respectively.

Semisynthetic Antibody Gene Fragments and Preparation of Mutants

Genes for antibody fragments may also be generated by semisynthetic methods known in the art (Barbas et al., 1992). Using the conserved regions of an antibody fragment as a framework, variable regions can be inserted in random combinations one or more at a time to alter the specificity of the antibody fragment and generate novel binding sites, especially in the generation of antibodies to antigens not conducive to immunization such as toxic or labile compounds. Along the same lines a known antibody sequence may be varied by introducing mutations randomly or site specifically. This may be accomplished by methods well known in the art such as mutagenesis with mismatched primers or error-prone PCR (Innir, 1990).

Functionally Equivalent Amino Acids

As previously discussed, modification and changes may be made in the structures of the signal or transversing proteins and peptides and still obtain a molecule having like, or otherwise desirable, characteristics. For example, certain amino acids may be substituted for other amino acids in a protein structure without appreciable loss of functional activity to transport the antibody, antibody fragment or peptide to the cell surface. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequences of the target and transversing proteins (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, such residues may not generally be exchanged.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (–0.4); threonine (–0.7); serine (–0.8); tryptophan (–0.9); tyrosine (–1.3); proline (–1.6); histidine (–3.2); glutamate (–3.5); glutamine (–3.5); aspartate (–3.5); asparagine (–3.5); lysine (–3.9); and arginine (–4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (–0.4); proline (–0.5±1); alanine (–0.5); histidine (–0.5); cysteine (–1.0); methionine (–1.3); valine (–1.5); leucine (–1.8); isoleucine (–1.8); tyrosine (–2.3); phenylalanine (–2.5); tryptophan (–3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid, as shown in Table 1.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

Materials and Methods

Bacterial Strains, Plasmids, and Growth Conditions

E. coli strain JM109 [endA1 recA1 gyrA thi-1 hsdR17 ($r_k$–, $m_k$+) relA1 supE44Δ(lac-proAB)/F' traD36 proAB lacI$^q$ lacZΔM15] was used for all studies. pTX101 codes for an Lpp-OmpA-β-lactamase fusion (Francisco et al., 1992). pTX152 codes for an Lpp-OmpA-scF$_v$(digoxin) fusion, where the scF$_v$(digoxin) is an anti-digoxin single chain F$_v$ consisting of the heavy- and light-chain variable regions (V$_H$ and V$_L$). The V$_H$ and V$_L$, joined by a 15 amino acid [(Gly)$_4$Ser]$_3$ linker (Huston et al., 1988), were amplified from messenger RNA isolated from two separate anti-digoxin hybridomas. An 11 amino acid peptide from the Herpes Simplex Virus glycoprotein (Novagen) was introduced at the C-terminus of the scF$_v$ for analytical purposes. pTX152 was constructed by first removing the bla from pTX101 by digestion with EcoRI and BamHI. The amplified gene coding for the anti-digoxin scF$_v$ was then digested with EcoRI and BamHI and ligated into pTX101. Both pTX101 and pTX152 carried the chloramphenicol resistance gene.

Cultures were grown in LB medium (Difco) supplemented with 0.2% glucose and chloramphenicol (50 μg/ml) at a temperature of either 24° C. or 37° C.

ELISA

Overnight cultures grown at 24° C. were harvested, resuspended in PBS at $OD_{600}$=2.0 and lysed by passage through a French pressure cell at 20,000 psi. The lysates were then diluted with 1 volume of phosphate buffered saline containing 2.0% bovine serum albumin (PBS/2% BSA) and 5 mM of the protease inhibitor phenylmethylsulfonyl fluoride (PMSF). 96 well microtiter plates were incubated overnight at 37° C. with 100 μl of 100 μg/ml of either bovine serum albumin (BAS) or digoxin-conjugated BSA (digoxin-BSA) in 0.1M sodium carbonate buffer (pH 9.2). All subsequent steps were carried out at room temperature. The wells were fixed for 5 min with 100 μl methanol and were then blocked for 45 min with 200 μl of pBS/1% BSA. After removing the blocking solution, the wells were incubated for 2 hr with 100 μl of lysates, washed 3 times with 200 μl PBS/0.1% Tween 20 and incubated for 1 hr with 100 μl/well of monoclonal antibodies against the HSV peptide or antiserum against β-lactamase. The wells were again washed 3 times with PBS/0.1% Tween, incubated for 1 hr with 100 μl of the appropriate secondary antibodies conjugated with horseradish peroxidase and were finally washed 5 times with PBS/0.1% Tween and 2 times with PBS. After addition of the substrate 2,2'-azino-bis(3-ethylbenzthiazoline-6-sulfonic acid) (Pierce, Rockford, Ill.) the absorbance of each well was measured at 410 nm.

Whole cell ELISAs were performed as described above except that 100 μl samples of overnight cultures that had been resuspended in PBS/1 BSA at $OD_{600}$=1.0 were used instead of cell lysates.

Fluorescence Microscopy and Fluorescence Activated Cell Sorting (FACS)

For fluorescence microscopy, overnight cultures grown at 24° C. were harvested, resuspended at $OD_{600}$=0.5 in PBS containing $10^{-7}$M fluorescein-conjugated digoxin (digoxin-FITC; ILS LTD, London) and were incubated at room temperature for 1 hr. Prior to microscopy the cells were washed once with PBS and resuspended in equal volumes of PBS and Vectashield mounting medium (Vector Laboratories) at an $OD_{600}$ of approximately 2.0.

Protein Measurements

The protein composition of whole cell membrane fractions isolated from overnight cultures was analyzed by SDS-PAGE on 12% acrylamide gels and by Western blotting using anti-HSV monoclonal antibodies obtained from Novagen Inc. (Madison, Wis.), and anti-OmpA antiserum. Whole membrane fractions were prepared as described in Francisco et al. (1992).

The following Examples are intended to illustrate the practice of the present invention and are not intended to be limiting. Although the invention is here demonstrated with a particular single chain antibody on the surface of E. coli, other forms of antibody molecules such as an $F_{ab}$, or $F_v$ could be used. Nor is the method limited to expression on an E. coli cell surface as it is contemplated that other host cells may also be used as numerous other gram negative organisms.

EXAMPLE 1
Surface Expression of Anti-digoxin Single Chain Fv Antibodies

A single chain $F_v$ specific for digoxin was constructed by PCR amplification of the $V_H$ and $V_L$, joined by a 15 amino acid [(Gly)$_4$Ser]$_3$ linker (Huston et al., 1989)760. A 33 residue sequence encoding an 11 amino acid peptide from the Herpes Simplex Virus glycoprotein (Novagen) was introduced at the C-terminus of the scF$_v$ for analytical purposes. The presence of the HSV peptide allowed detection of the scF$_v$(digoxin) protein by reaction with a monoclonal antibody specific for the 11 amino acid epitope. The sequence of the single chain $F_v$ antibody fragment is disclosed in FIG. 1 (SEQ ID NO: 1).

The gene encoding the scF$_v$(digoxin) antibody was ligated in frame to lpp-ompA(46–159) from plasmid pTX101 (Francisco et al., 1992), as follows: First, the bla from plasmid pTX101, which encodes an Lpp-OmpA(46–159)-β-lactamase fusion was excised by digestion with EcoRI and BamHI. The amplified gene coding for the scF$_v$(digoxin) was then digested with EcoRI and BamHI and ligated into pTX101. The resulting plasmid designated pTX152 was identical to pTX101 except that the bla gene of pTX101 was substituted with the scF$_v$(digoxin) fragment. Both pTX101 and pTX152 carry the chloramphenicol resistance gene for antibiotic selection of transformants.

E. coli JM109 was transformed with pTX152 and transformants were selected on plates containing chloramphenicol. Using a single transformant colony, the presence of the Lpp-OmpA(46–159)-scF$_v$(digoxin) fusion was confirmed by restriction analysis and DNA sequencing.

Cells were grown in liquid culture at 37° C. and used to isolate total membranes. The presence of a band of the expected size (42 kDa) was detected in Western blots of whole cell membranes probed with antibodies specific for OmpA and for the HSV peptide (FIG. 2A). Cells containing pTX152 produced a protein which reacted with both the HSV-specific and the OmpA specific sera, as expected for the Lpp-OmpA-scF$_v$(digoxin) fusion. Control cells containing pTX101 reacted only with OmpA antiserum. The lower molecular weight band in lanes 1 and 2 corresponds to the intact OmpA protein of E. coli.

The near absence of lower molecular weight bands cross-reacting with either the anti-HSV or the anti-OmpA antibodies indicated that the scF$_v$(digoxin) was not subjected to proteolysis ostensibly because it was anchored on the cell surface and consequently is physically separated from intracellular proteases. The intensity of the Lpp-OmpA(46–159)-scF$_v$(digoxin) band in FIG. 2A is comparable to that of the native OmpA band. The latter is a highly expressed protein that is present in the E. coli outer membrane at about 100,000 copies per cell (Lugtenberg & Van Alphen, 1983). The level of expression Lpp-OmpA(46–159)-scF$_v$(digoxin) is on the order of 50,000–100,000 copies per cell.

EXAMPLE 2

This Example describes the surface display and screening of antibody libraries generated by PCR amplification of mRNA from spleen cells of mammals immunized with the desired antigen. The Example describes how the display of recombinant antibody libraries on the cell surface and the screening of such libraries by fluorescently activated cell sorting can be used to identify clones that bind to the desired antigen with high affinity and thus constitutes and in vitro replacement of hybridoma technology.

Construction and Screening of an Ab library generated by PCR amplification of spleen mRNA Balb/c mice were immunized with digoxin using standard protocols (Harlow & Lane, 1988). After at least two booster injections, antiserum was collected and the titer of the antibody response towards digoxin was determined by ELISA assays. Mice exhibiting high anti-digoxin titers were sacrificed and the intact spleens were removed and used to extract mRNA (Sastry et al., 1989). The spleen mRNA was subsequently used as template for PCR amplification using primers complementary to constant and variable domain framework regions of different antibody subclasses.

Separate rounds of PCR amplification were employed to amplify $V_H$ and $V_L$ sequences. PCR products of the expected molecular weight were purified following electrophoresis on agarose gels, digested with ScaI and ligated to give a gene encoding a full length gene encoding the sequence $V_H$-[(Gly)$_4$-Ser]$_3$-$V_L$-(HSV tag). Subsequently, the ligated DNA was treated with EcoRI and BamHI and was ligated to the large EcoRI-BamHI fragment of pTX101. The resulting DNA was used to transform DH10b cells by electroporation. The electroporation mixture was used to inoculate shake flasks with LB media containing chloramphenicol. After growth for several generations at 24° C. the cells were harvested by centrifugation and used for fluorescently activated cell sorting.

Enrichment of cells displaying scF$_v$(digoxin) by FACS

Antibody expressing cells were sorted essentially quantitatively from a moderate excess of control E. coli in a single step. Specifically, in mixtures containing JM109/pTX101 control cells at an excess of either 100:1 or 1,000:1, the fraction of the total population that was sorted in the high fluorescence intensity window was 1.1% and 0.1% respectively (after subtracting the background), as expected from the ratio of input cells.

The use of FACS for isolating rare clones from a very large excess of background was evaluated. JM109/pTX101 and JM101/pTX152 were mixed at a ratio of 100,000:1 and labeled with digoxin-FITC. Following washing to remove any non-specific binding of the digoxin-fluorescein conjugate on the control E. coli, 500,000 cells were run through the FACSort flow cytometer. A wide sorting gate, i.e., the minimum fluorescence required for acceptance of an individual cell, was selected such that up to 0.2% of the control cells fell within the sorting window. This ensured that all the scF$_v$(digoxin) expressing cells would be recovered. The cells having an allowable fluorescence signal were collected and grown in fresh media at 37° C.

An aliquot from that culture was used to inoculate fresh media and incubated at 24° C. Cells grown at this lower temperature were used for FACS because of the higher extent of surface display of the scF$_v$(digoxin) antibody on the surface of cells grown at 24° C. 500,000 cells from this culture were run again through the FACSort and those with a fluorescence within the allowable window were collected automatically under sterile conditions. The sorted population was grown first at 37° C. and then subcultures at 24° C. and was subjected to a final round of sorting as above.

Figure 4A:
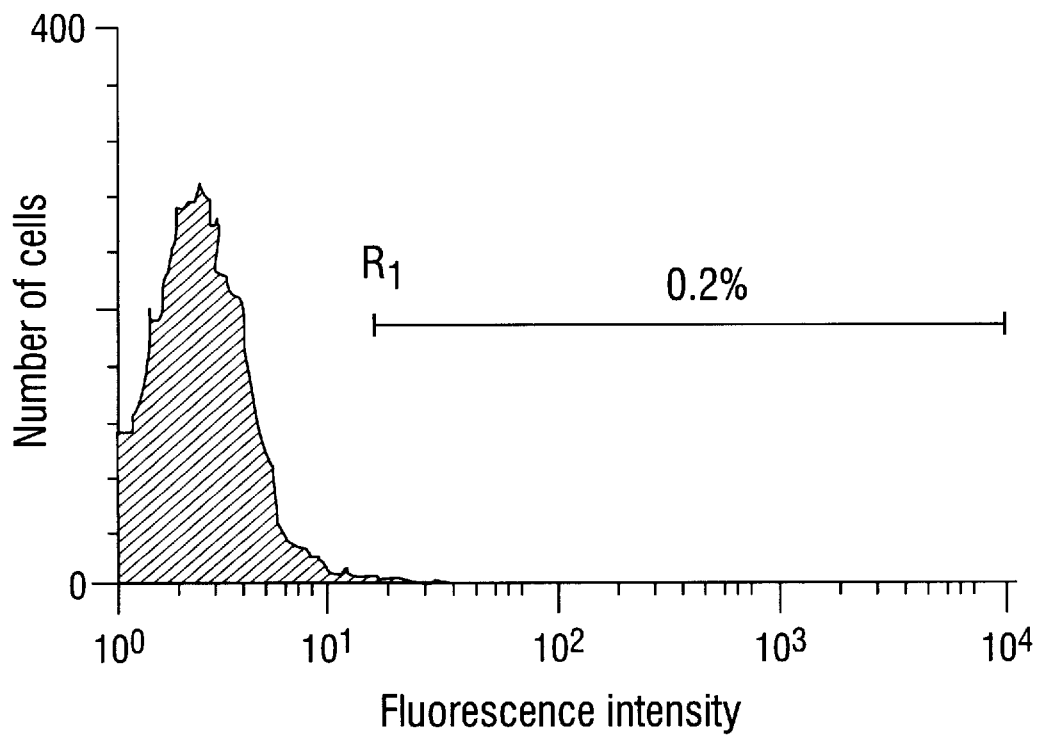
FIGS. 4A–4G. Histogram data from FACS. The bar in each graph represents the sorting gate or the fluorescence intensity defined as a positive event. The sorting gate was chosen to maximize the number of positive events while minimizing the number of negative events within the window. All samples were labeled with 10 −7M digoxin FITC.
Figure 4B:
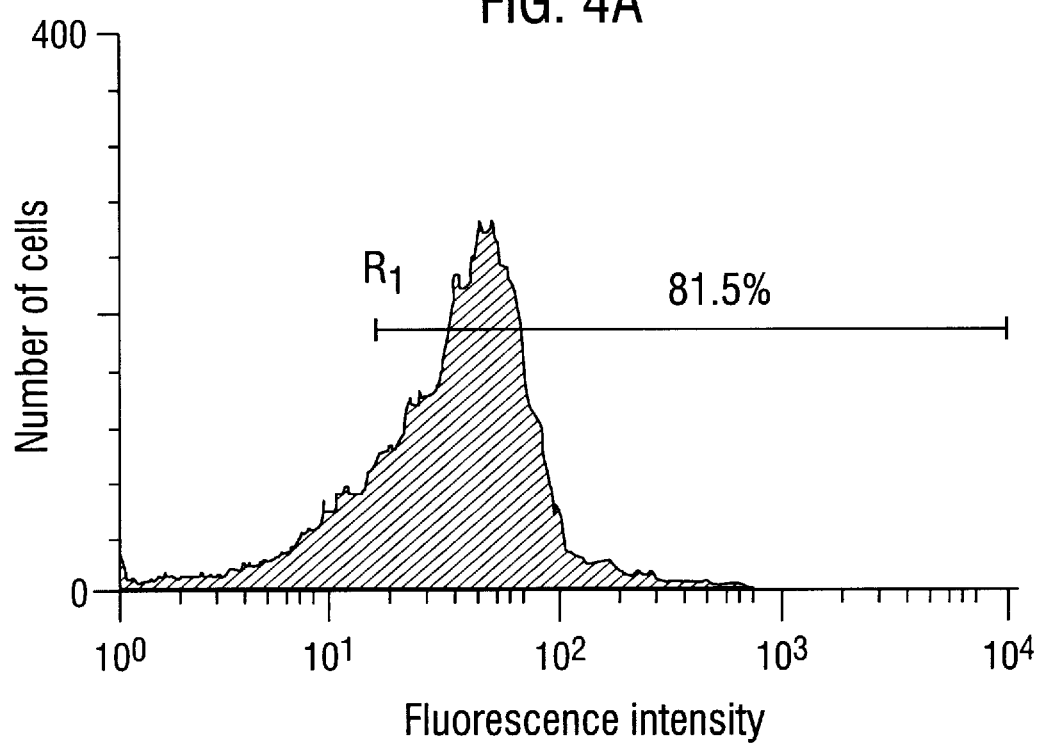
Figure 4C:
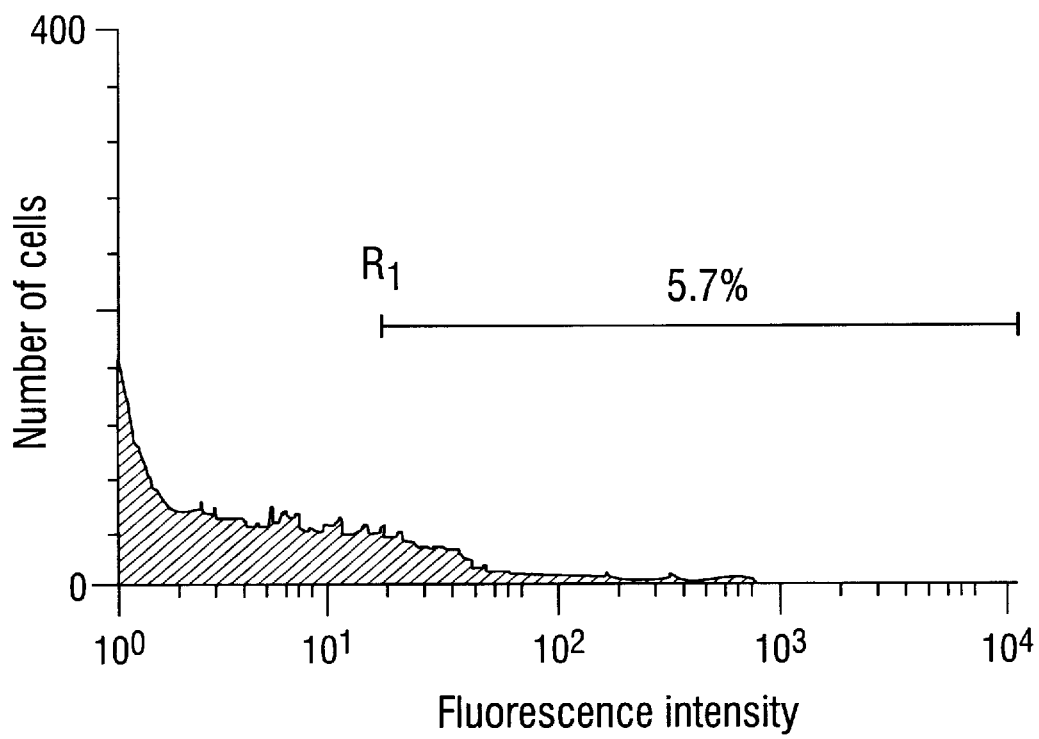

To ensure the complete absence of artifacts due to non-specific cell adhesion in the flow path of the FACSort, each run was followed by extensive washing with bleach. FIG. 4E, FIG. 4F and FIG. 4G show the cell fluorescence distribution for the sorting runs. After only two rounds of growth and sorting, the fluorescence intensity of 79% of the cell population fell within the positive window. A similar enrichment was reproducibly obtained in three independent studies. These results were not due to a growth advantage of the cells expressing Lpp-OmpA(46–159) -scF$_v$(digoxin), since successive regrowth of the input cell mixture in the absence of sorting did not result in any detectable enrichment.

To verify that the cells with the increased fluorescent signal after the final sorting step were indeed JM109/pTX152, a sample of cells from the final round of FACS was plated on chloramphenicol plates and then replica plated on plates containing 100 µg/ml ampicillin. The pTX152 plasmid confers resistance only to chloramphenicol whereas the plasmid pTX101 which is present in the control cells also confers resistance to ampicillin. Over 95% of all the colonies examined were chloramphenicol resistant and ampicillin sensitive (cm$^+$, amp$^-$) consistent with the phenotype expected for JM101/pTX152 cells. As an additional test, plasmid DNA was isolated from eight cm$^+$, amp-colonies and the presence of pTX152 was confirmed by restriction analysis.

The above results demonstrate that E. coli displaying a recombinant antibody on its surface can be recovered from at least a $10^5$-fold excess of control E. coli simply by incubation with a fluorescent hapten and fluorescent activated cell sorting. Only two rounds of sorting and regrowth of the sorted cell population are needed for enrichment from a large excess of background. Sorting is both rapid and efficient. Using a low-end flow cytometer it is possible to sort $1 \times 10^6$ cells per hour when operated so that the cells pass through the laser beam single file. Higher sorting rates can be obtained with a larger model (up to $5 \times 10^7$ cells per hour) and even higher still by sorting multiple cells at a time (at the expense of increased background that one would expect to be eliminated by resorting the selected population). In addition, the sorting of positive clones is essentially quantitative and is limited only by the accuracy of the flow cytometer which is of the order of 95% (Tanke & van der Keur, 1992.)

Screening of an Antibody Library Generated by Random Mutagenesis

The inventors contemplate the use of random mutagenesis to create an antibody library. Such a library might include antigen binding domains of a known antibody or antibodies that have catalytic properties.

The majority of specific contacts to bound hapten involve residues in the CDR 3 of both chains (Kuby, 1991). The key contact residues for the F$_{ab}$ portion of the 26–10 anti-digoxin antibody/digoxin complex (Schildbach et al., 1993) have been determined from the x-ray crystal structure. As expected, these key contact residues are in the CDR 3 of both chains.

PCR with degenerate oligonucleotide primers was employed to mutagenize the CDR 3 of both the heavy and light chains of the scF$_v$ digoxin antibody. Many of the different techniques for PCR mutagenesis that have been reported (Innis, et al, 1990; Morrison & Desrosiers, 1993; Aiyar & Leis, 1993) would be useful for this strategy. The primers, as shown in FIG. 5, were designed to introduce random codons at the key contact residues. A library of $1.6 \times 10^4$ was generated.

The new library will be screened for mutants binding to haptens such as trityl (triphenylmethyl) using a trityl-fluorescein conjugate. Sorting with fluorescein-fluorescein conjugate will also be employed as a control to ensure that clones binding the fluorescein-trityl conjugate have specificity towards the trityl moiety. Cells that sort in the positive window following incubation with the Texas Red-fluorescein conjugate and in the negative window when screened with the trityl-fluorescein conjugate will be selected for further studies. Libraries can be generated from virtually any antibody sequence from which the gene is cloned.

While it is advantageous to know the key contact residues, a random mutagenesis of CDR 3 for one or both chains may also be used to generate libraries. The resulting libraries can then be screened for compounds where the antibody is difficult to generate by conventional means such as toxic or chemically labile compounds.

This strategy will also be useful to generate human antibodies for immunotherapy. A human antibody may be subjected to mutagenesis and the resulting library screened for antibodies against a particular antigen. This is a particularly important strategy since it is not general practice to immunize humans with potentially dangerous compounds for the production of antibodies. Laboratory animals such as mice or rabbits will be hyperimmunized with a selected antigen and the antibodies isolated from the spleen which is a rich source of antibody producing cells. However, even those compounds used to generate antibodies in humans can only be isolated in relatively small quantities from peripheral blood. Many attempts have been made to reproduce monoclonal antibodies in humans (Persson et al., 1991; Mullinax et al., 1990) including the production of humanized antibodies that have been generated (Winter & Milstein, 1991) using a mouse variable loops on human constant regions. Significant problems may arise when a modified antibody is placed in a human due to the presence of non-human sequences within the construct.

The antibodies generated using the methods disclosed by the inventors will have a distinct advantage over previously reported methods of generating human antibodies in that the antibody will have the entire sequence derived from a human source.

EXAMPLE 3
Surface Expression of Anti-digoxin incorporating a Protease Cleavage Site A construct similar to that used for surface expression of $scF_v$ (digoxin) can be modified to incorporate a protease cleavage site. For example, the recognition sequence of enterokinase [$(Asp)_4$-Ile-Arg] can be introduced in the Lpp-OmpA(46–159)-$scF_v$ between the OmpA(46–159) and the $scF_v$ domains. The protease cleavage site at the N-terminal of the $scF_v$ antibody domain of the fusion protein is then used to release the $scF_v$ antibody in soluble form following treatment of the cells with the appropriate proteolytic enzyme. Because the outer membrane of *E. coli* serves as a protective barrier to the action of externally added proteases, very few contaminating proteins will be present in the culture supernatant. A single colony expressing a desired single chain $F_v$ antibody can be grown in liquid media and harvested by centrifugation after overnight growth at 24° C. The cells are resuspended in buffer to maintain the pH approximately neutral. Protease added at appropriate concentrations to the fusion protein to be treated and incubated at least 4 hours at 4° C. will release the soluble single chain $F_v$. Subsequently the cell suspension is centrifuged and the supernatant containing the solubilized single chain $F_v$ antibody is collected.

To separate the cleaved, soluble $scF_v$ antibody from the protease, as well as any *E. coli* trace contaminants, a $His_6$ sequence may be introduced at the C-terminus of the $scF_v$ using PCR amplification with the appropriate primers. Polyhistidine tails bind strongly to metals so that the fusion protein can be purified by immobilized metal-ion affinity chromatography (IMAC). The separation of the cleaved $scF_v$ antibody using is carried out as described by Georgiou, et al (1994).

Lpp-OmpA(46–159) fusions are typically expressed at a high level, typically around $5 \times 10^4$ per cell. Thus the yield after protease treatment and IMAC is at least 2–3 mg of antibody per liter of shake flask culture.

EXAMPLE 4

The success of the immunoassay described in Example 1 is dependent on the exposure of antibody binding site as it is expressed on the bacterial cell surface. As the data in this example indicate, the single chain digoxin antibody expressed on the surface of *E. coli* has a binding affinity for digoxin that is at least within an order of magnitude of the reported binding constant for soluble anti-digoxin $scF_v$.

Exposure of $scF_v$ binding site when expressed on cell surface

The $scF_v$ domain of the Lpp-OmpA-$scF_v$(digoxin) fusion protein encoded by pTX152 was shown by ELISA to bind specifically to the hapten digoxin. Whole cell lysates from JM109/pTX152 and from JM109/pTX101 as control were incubated on microtiter wells that had been coated with either digoxin-conjugated BSA (digoxin-BSA) or unconjugated BSA. Subsequently, the wells were treated with antibodies against the HSV peptide or β-lactamase to detect Lpp-OmpA(46–159)-$scF_v$(digoxin) or Lpp-OmpA(46–159)-β-lactamase, respectively. FIG. 2A shows that lysates from JM198/pTX152 bound specifically to wells coated with digoxin-BSA but not to unconjugated BSA, whereas the lysates from the control strain, JM109/pTX101, did not give a signal with either. Thus, Lpp-OmpA(46–159)-$scF_v$ (digoxin) is active and can bind to the hapten specifically.

Figure 2B:
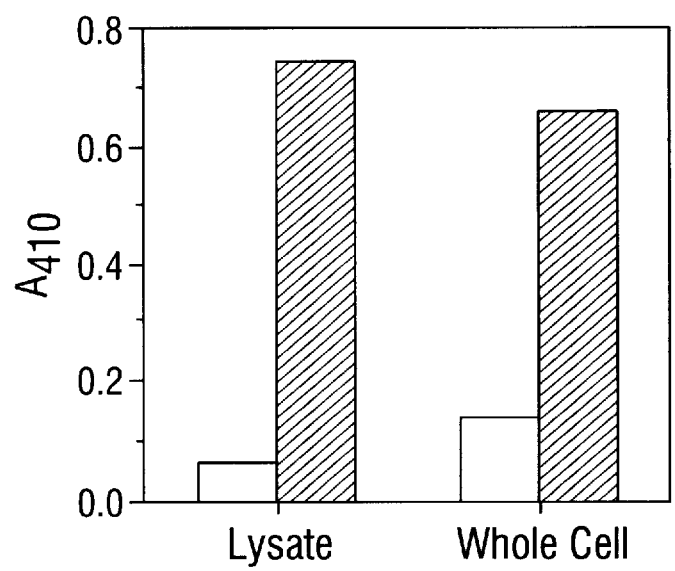
FIG. 2B. Lysate and whole cell ELISAS of JM109 cells containing plasmid pTX101 (solid) or pTX152 (hatched). Samples were incubated on microtiter wells coated with digoxin-conjugated BSA and probed with anti-β-lactamase (pTX101) or anti-HSV (pTX152) antibodies. Absorbance readings were referenced to wells that were untreated with either lysates or whole cells.

FIG. 2B shows the results of ELISAs using intact cells. Samples containing the same number of cells were used in all the studies. Cells containing the control plasmid, pTX101, gave the same low signal when incubated on microtiter wells coated with either unconjugated BSA or with digoxin-BSA. A similar weak signal was detected with JM109/pTX152 incubated on BSA-coated wells and is presumably due to non-specific binding. In contrast, a much higher absorbance was evident in wells coated with the digoxin-BSA conjugate indicating that there are active fusion protein molecules on the cell surface.

Figure 3A:
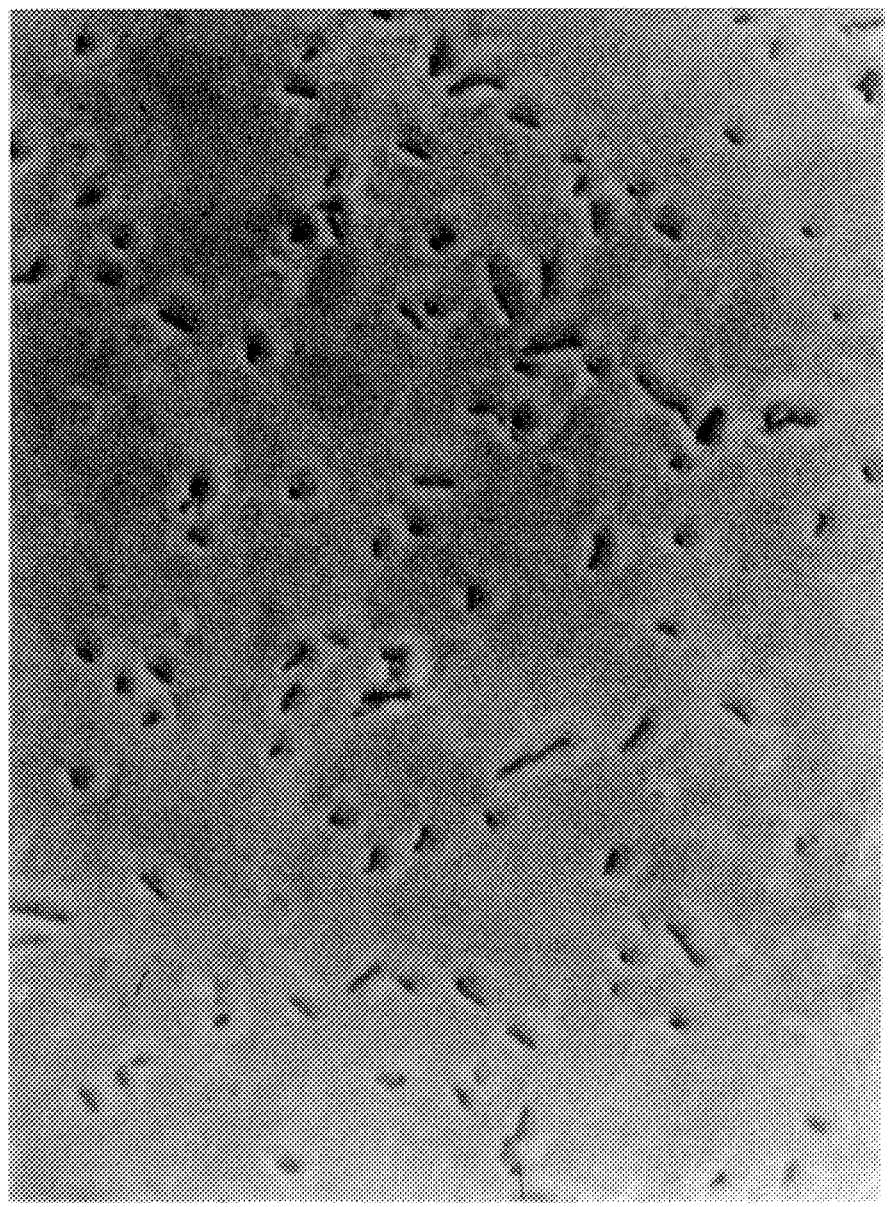
FIG. 3A. Phase contrast micrograph of JM109/pTX152 cells after 1 hr of incubation with $10^{-7}$M digoxin-FITC.
Figure 3B:
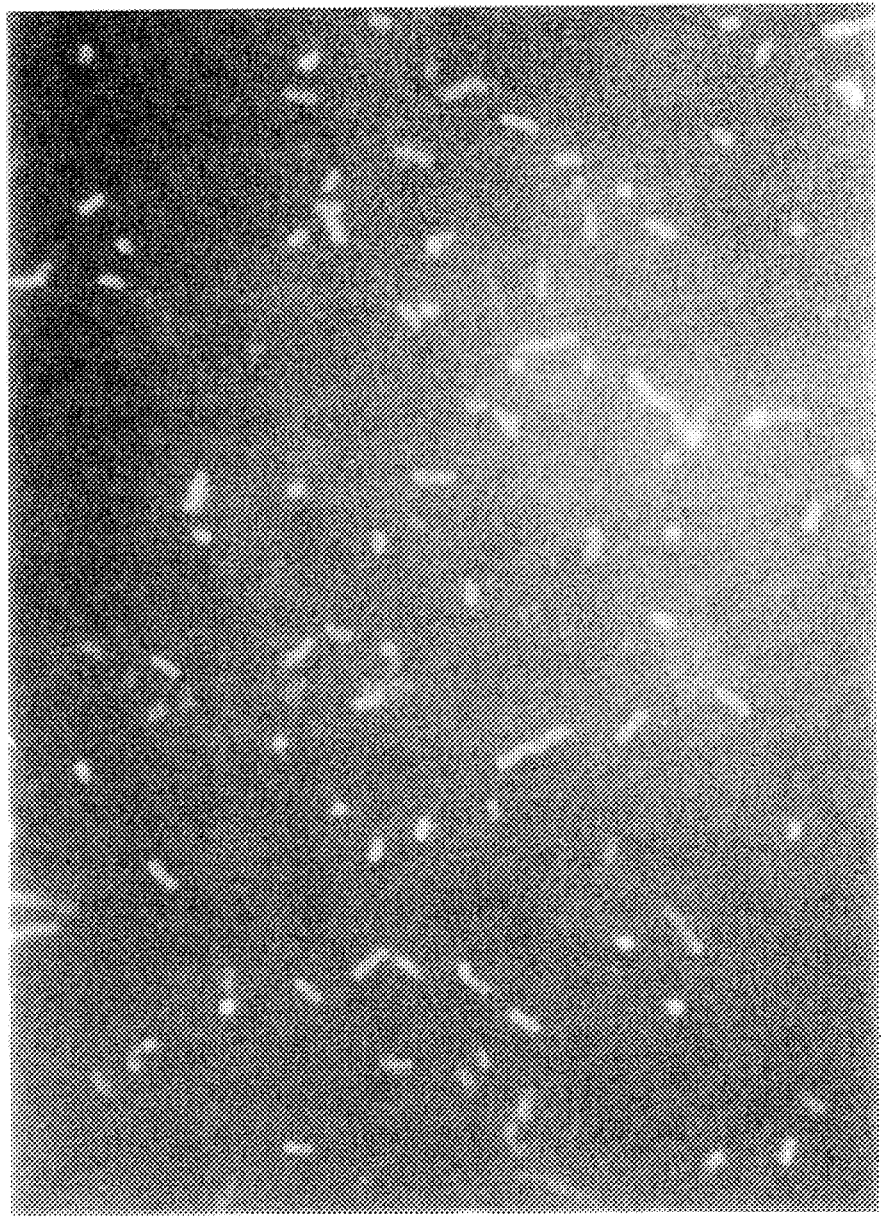
FIG. 3B. Micrographs of the same field as in FIG. 3A of JM109/pTX152 cells after a 1 hour incubation with $10^{-7}$M digoxin-FITC.

The display of the active $scF_v$ antibody on the cell surface was confirmed by fluorescence microscopy (FIG. 3B). JM109/pTX152 cells were grown overnight at 24° C., incubated with a $1 \times 10^{-7}$M solution of a digoxin-FITC conjugate for 1 hour and washed. As shown in FIG. 3A and FIG. 3B, all of the cells visible with phase contrast microscopy gave a strong fluorescence signal. In control studies, when JM109/pTX101 cells were incubated with the same concentration of digoxin-FITC and then washed, none of the cells became fluorescently labeled. Furthermore, protease treatment drastically reduced the ability of the cells to bind fluorescein-digoxin judging from the generation of a signal detectable by FACS.

The intensity of the fluorescence signal from JM109/pTX152 was dependent on the cell growth temperature and was much higher for cultures grown at 24° C. instead of 37° C. This was consistent with previous results showing that the amount of proteins expressed on the surface of *E. coli* by fusion to Lpp-OmpA(46–159) increased as the temperature is decreased (Francisco et al., 1992; 1993). Assuming that the efficiency of surface display in this case is similar to that of β-lactamase (Francisco et al., 1992), then at 24° C. virtually all the $scF_v$ antibody chains must be accessible on the cell surface.

Specific binding of surface expressed $scF_v$ with labeled antigen Samples of $10^8$ cells per ml from cultures grown at 24° C. were incubated with digoxin-FITC at $10^{-7}$M, washed in buffer and diluted to $3 \times 10^6$ cells per ml prior to sorting. The samples were then analyzed using a FACSort flow cytometer. FIG. 4A and FIG. 4B show that the fluorescence intensity of JM101/pTX152 cells expressing a surface displayed recombinant antibody specific for digoxin was substantially higher than the intrinsic background signal of control *E. coli* cells. [In the case JM101/pTX101 expressing Lpp-OmpA(46–159)-β-lactamase is used as a control].

Figure 4D:
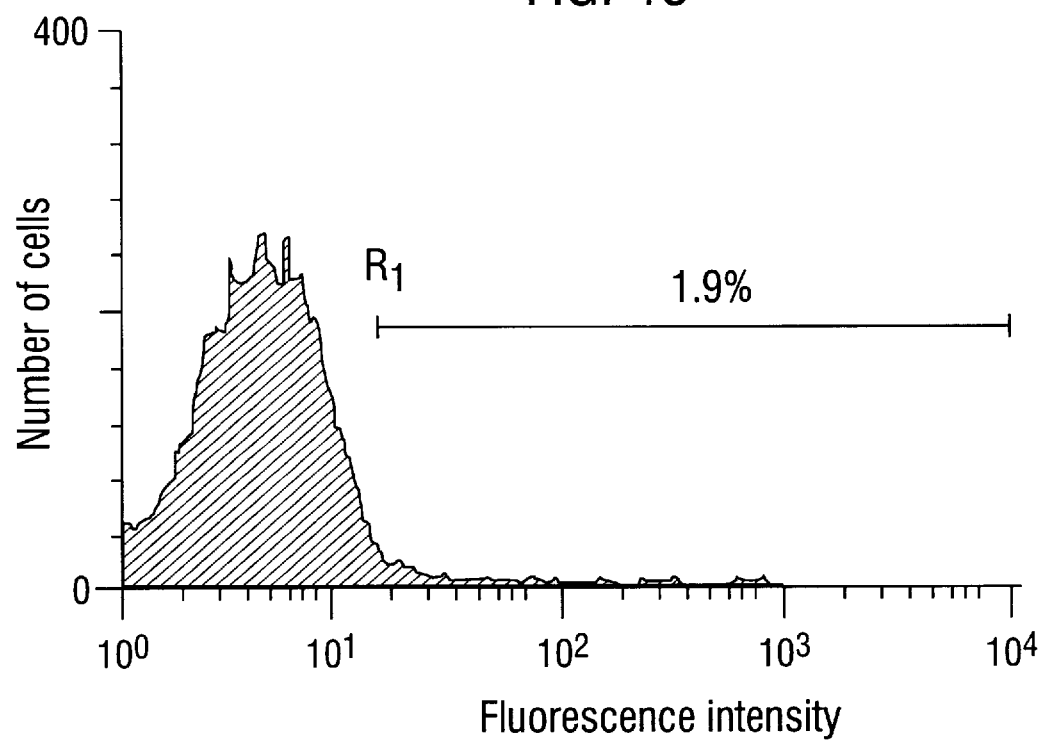
Figure 4E:
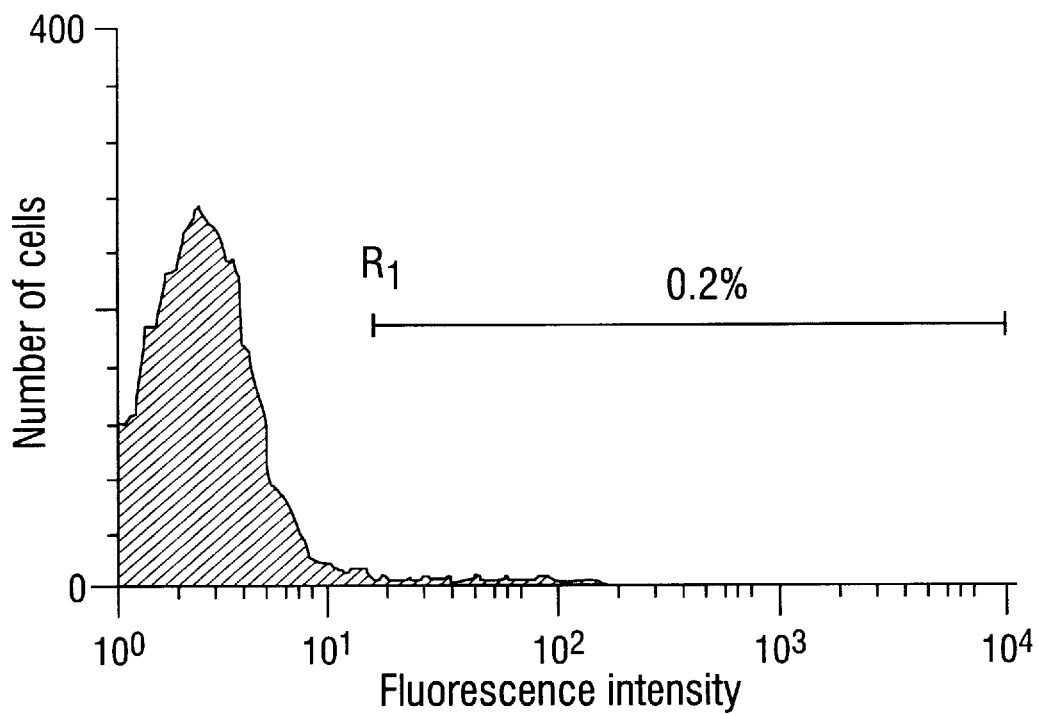
Figure 4F:
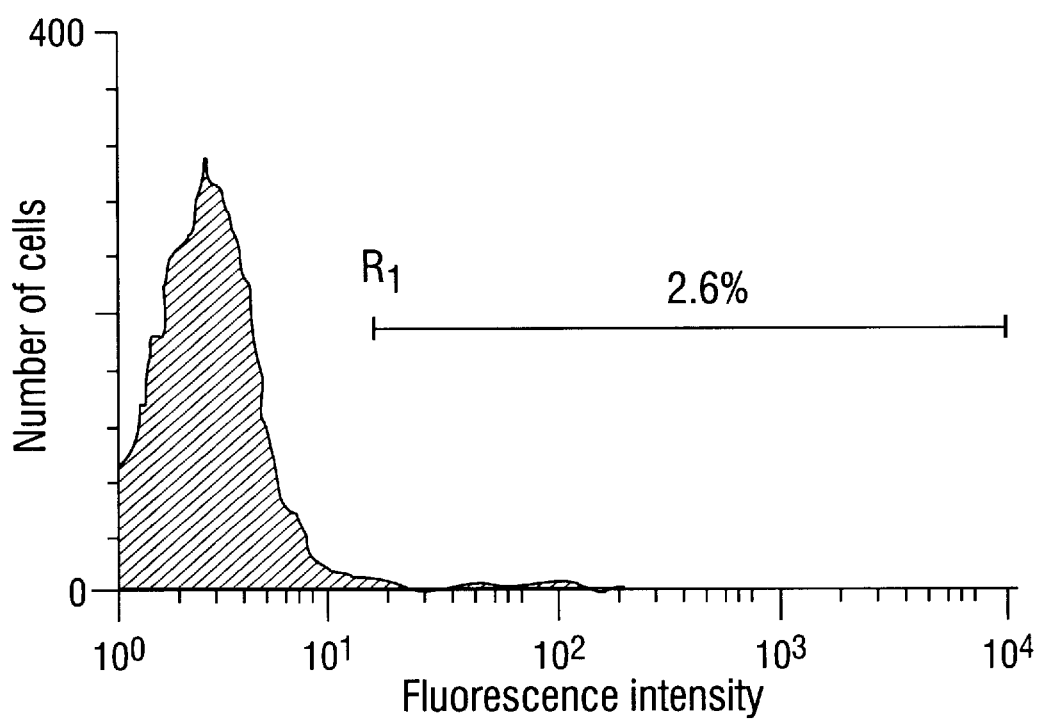
Figure 4G:
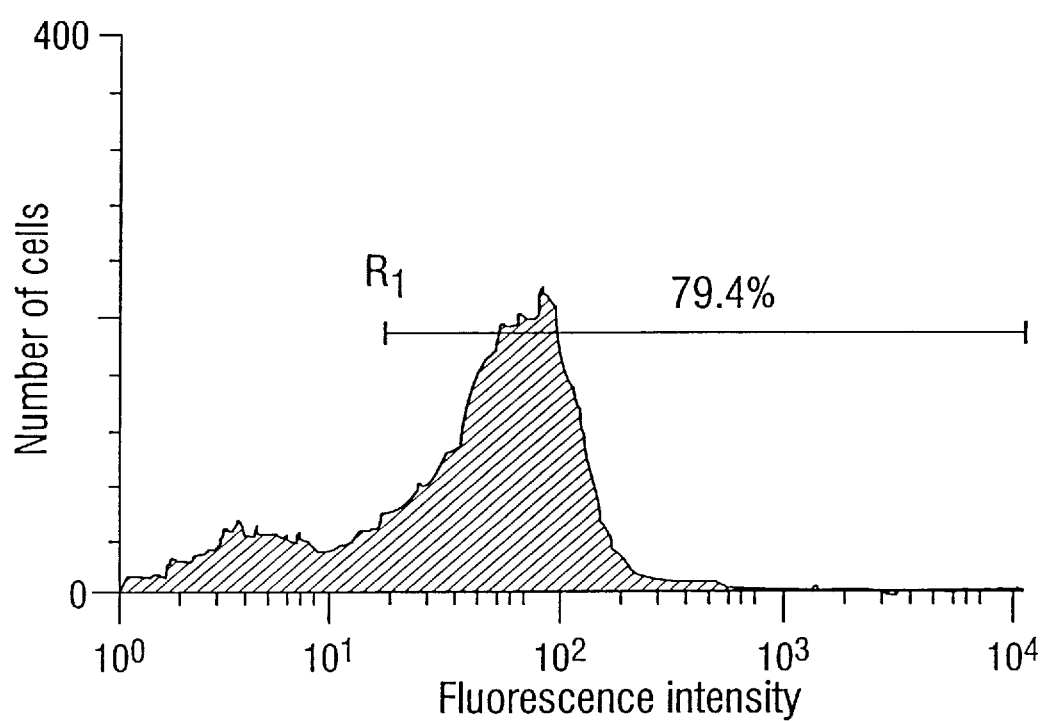

When JM109/pTX152 cells were preincubated with an excess of free digoxin prior to incubation with the digoxin-FITC conjugate, the fluorescence intensity of the cells was the same as for the background (FIG. 4D). This specific inhibition was also seen using fluorescence microscopy, and demonstrates that the surface expressed scF$_v$(digoxin) specifically binds the fluorescently labeled hapten in the binding site and is not the result of nonspecific interactions.

Treatment of intact cells with trypsin prior to incubation with digoxin-FITC almost completely eliminated the population of fluorescently labeled cells detected by flow cytometry (FIG. 4C). In gram-negative bacteria, the outer membrane serves as a barrier to preclude the diffusion of large extracellular molecules such as proteins. The action of trypsin is limited to the proteolysis of proteins exposed on the external surface of *E. coli* (Kornacker & Pugsley, 1990). Thus, the above result provides further evidence that the active scF$_v$(digoxin) is indeed accessible on the outer surface, free to interact with molecules in solution.

The scF$_v$(digoxin) binding sites appeared to be fully saturated at concentrations of digoxin-FITC above $10^{-7}$M. Appreciable fluorescent signal was clearly detected even at digoxin-FITC concentrations of $10^{-9}$M. These results are consistent with a binding constant that is at least within an order of magnitude of the reported affinity of a soluble anti-digoxin scF$_v$ antibody (Huston et al., 1988).

The specific fluorescence of cells expressing Lpp-OmpA (46–159)-scF$_v$(digoxin) was at least 40 times higher than that of control cells.

EXAMPLE 5

This Example illustrates a solid phase immunoassay using *E. coli* with anti-digoxin single chain F$_v$ displayed on the surface. This immunoassay is demonstrated to be a sensitive and quantitative technique. To facilitate the removal of the surface expressed antibody following the reaction with antigen, the cells may be attached to a solid support such as a membrane, dipstick or beads.

Solid Phase Immunoassays

Digoxin-FITC (The Binding Site Inc. (San Diego, Calif.) was diluted to a concentration of 20nM in PBS. Digoxin (Sigma, St. Louis, Mo.) was brought to a concentration of 1 μM in PBS.

The pTX152/JM109 cells were grown in LB overnight at 37° C. then subcultured into fresh LB and grown overnight at room temperature. The cells were harvested and resuspended in PBS pH 7.4 at a concentration of $10^{10}$ cells/ml, based on the O.D.$_{600}$ to form a cell stock. Some cells were also resuspended in 15% glycerol/water and stored at 70° C. Frozen cells yielded the same results as freshly prepared cells.

The following reagents were transferred to a 1.5 ml microcentrifuge tube, 25 μl of 20 nM digoxin-FITC solution, 0.5–50 μl of 1 μM digoxin and PBS to a final volume of 950 μl. The mixture was vortexed briefly and pulsed in an Eppendorf microcentrifuge. A 25 μl or 100 μl aliquot of the cell stock ($10^{10}$ cells/ml) was added to the mixture and allowed to incubate for 1 hour at room temperature. Following this incubation the cells were spun in a microcentrifuge for 5 minutes at 5,000 rpm and the supernatant collected. The fluorescence of the digoxin-FITC in the supernatant was measured using a fluorimeter.

This immunoassay was also performed with the cells attached to a solid support. The solid support was Fisher filter paper P5 was cut into strips approximately 0.5 cm×2 cm, and dampened in PBS by submerging one end of the filter paper and allowing it to move upward. The filter paper was allowed to dry slightly and 10 μl of a solution containing 6×10$^9$ cells/ml was applied to the filter paper. The cells were fixed to the paper with a solution of 6-PLP, 8% PFA and NaIO$_4$. The 6-PLP solution is 10 mM 6-PLP, 200 mM MES, 700 mM NaCl, 50 mM KCl, 700 mM Lysine-HCl, 50 mM MgCl$_2$, and 70 nM EGTA followed by 0.01M MgCl$_2$ and 8% PFA. The 8% PFA was prepared by addition of 4 g of PFA into 50 ml of water, followed by heating the solution to 70° C. with constant stirring. Approximately 2 drops of a 1M solution of NaOH was added to the solution until it became clear. The solution was then filtered through Whatman filter paper #1, allowed to cool and stored at 4° C. until use. The final fixative solution was produced by mixing the components A, B and C to a final volume of 10 ml just prior to use, where A is 1 ml 6-PLP, 04 g sucrose and 3.03 ml water; B is 21.4 mg NaIO$_4$; and C is 4.62 ml 8% PFA. The fixative was applied dropwise to one end of the filter paper and allowed to soak upwards. The excess fixative was allowed to drain and the filter paper was washed twice with a solution of 100 mM NH$_4$Cl. The filter paper can then be stored in a solution of PBS until use.

The assay was performed by removing the filter paper with the cells attached and then measuring fluorescence of the solution.

Essentially quantitative assays for an antigen can be run using a mixture of a known amount of labeled antigen combined with an unknown amount of unlabeled antigen. In one exemplary study, pTX152/JM109 with antidigoxin antibody displayed on the surface were grown in LB overnight at 37° C., subcultured into fresh LB and grown overnight at room temperature. The cells were pelleted and resuspended in PBS to form a stock solution of cells at a concentration of 1×10$^{10}$ cells/ml. A mixture of 25 μl of 20 nm digoxin-FITC and an amount of 1 μM free digoxin in the range of 0.5–50 μl, was prepared and brought to a final volume of 950 μl with PBS. A 25 μl or a 100 μl aliquot of the cell stock solution was added to the mixture to give a total of 0.25×10$^9$ or 1×10$^9$ cells. The mixture was then allowed to incubate at room temperature for 1 hour. The cells were pelleted and the fluorescence of the supernatant was measured for each sample.

Figure 6:
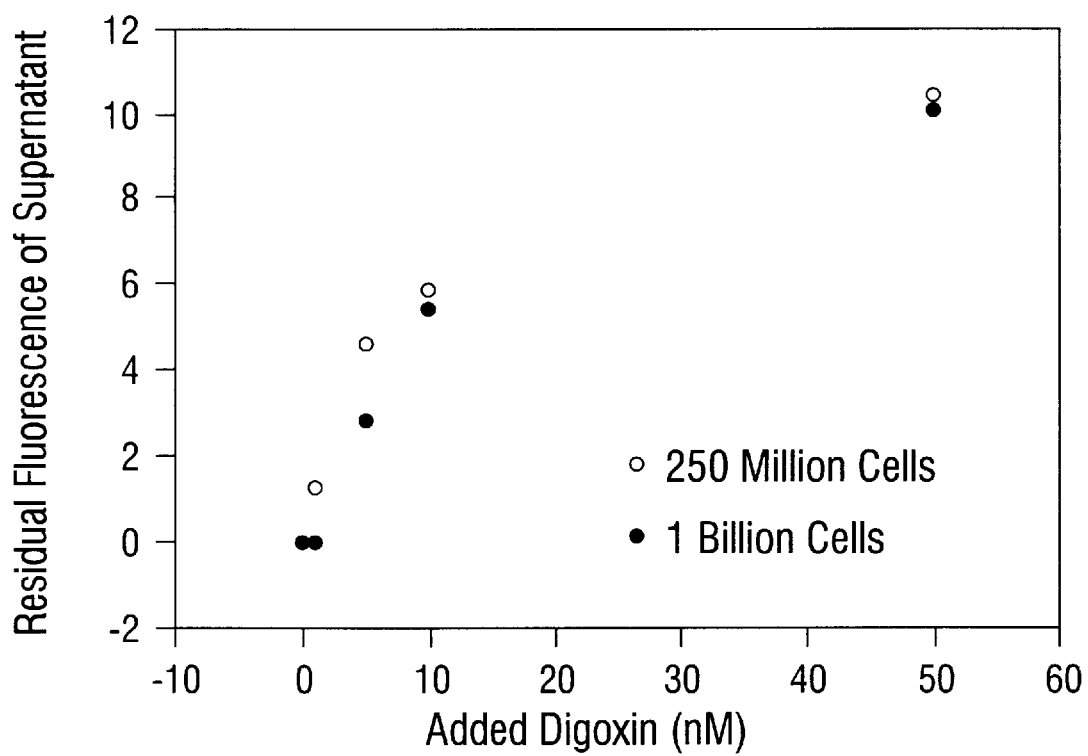
FIG. 6. Whole cell immunoassay using 0.5 nM FITC labeled digoxin.

FIG. 6 shows a plot of the residual fluorescence observed with the indicated amount of free digoxin, 0.5 nM digoxin-FITC conjugate and either 250 million or 1 billion cells expressing the antidigoxin single chain antibody on their surface.

To facilitate the removal of the surface expressing antibody cells following the reaction, the cells may be attached to a solid support. In this example the solid support consisted of a membrane however many other supports would work as well such as dipsticks or beads.

Strips of filter paper were moistened with PBS and allowed to dry slightly. A 10 μl aliquot of a 6×10$^9$ cells/ml of a cell suspension containing pTX152/JM109 cells displaying anti-digoxin antibodies on their surface was applied to the strips of pre-moistened filter paper. The cells were then fixed to the paper using a mixture of 6-PLP, PFA and NaIO$_4$, as described in the materials and methods, and washed twice with a solution of 100 mM NH$_4$Cl. Following the incubation no centrifugation is necessary the filter paper is simply removed from the solution and the residual fluorescence measured as described previously.

The assays described in this example use fluorescence as the indicator of binding; however, other indicator reactions may be used such as radioactivity, enzyme conjugates and when the surface expressed antibody is catalytic, an assay for catalytic activity may be used.

EXAMPLE 6

Electrochemiluminescence Detection

Electrochemiluminescence (ECL) is also contemplated as a detection technique for immunoassays. ECL involves the indirect electrochemical excitation of certain molecules, usually Ru(bipy)$_3^2$+ derivatives, that then relax back to ground state by emitting light. The amount of light is measured, thus providing a quantitative assay. There are some advantages of ECL detection. First, the electrode can be tuned to different potentials so that only the desired molecules can be excited, even in the presence of many different chemical species. Second, since the ECL measurements are carried out in the dark, there is no background signal of light. Thus, ECL, like regular chemiluminescence, is highly sensitive (down to 200 fmol/L have been detected) (Blackburn et al., 1991).

Except for the use of an electroluminescent molecule, the procedures are analogous to the procedures for competitive immunoassays described in Example 1. An analyte molecule is covalently attached to Ru(bipy)$_3^2$+. Known amounts of this conjugate will then be used in competition studies with the unknown sample of the analyte. Following equilibration and removal of cells (simple centrifugation of cells or removal of dipstick, beads, etc.), ECL will be used to quantitate the Ru(bipy)$_3^2$+ left in solution. This quantity will be proportional to the amount of analyte in the original unknown solution.

REFERENCES

The following references, to the extent that they provide exemplary procedural or other details supplementary to those set forth herein, are specifically incorporated herein by reference.

Aiyar & Leis, "Modification of the Megaprimer Method of PCR Mutagenesis: Improved Amplification of the Final Product," *BioTechniques*, 14:366–369, 1993

Antibodies: A Laboratory Manual, Cold Spring Harbor Laboratory, 1988

Barbas et al., "Assembly of combinatorial antibody libraries on phage surfaces: The gene III site," *Proc. Natl. Acad. Sci. USA*, 88:7978–7982, 1991

Barbas et al., "Semisynthetic combinatorial antibody libraries: A chemical solution to the diversity problem," *Proc. Natl. Acad. Sci. USA*, 89:4457–4461, 1992

Better et al., "*Escherichia coli* Secretion of an Active Chimeric Antibody Fragment," *Science*, 240:1041–1043, 1988

Blackburn et al., "Electrochemiluminescence Detection for Development of Immunoassays and DNA Probe Assays for Clinical Diagnostics," *Clinical Chemistry*, 37 (9):1534–1539, 1991

Campbell, in: *Monoclonal Antibody Technology, Laboratory Techniques in Biochemistry and Molecular Biology*, Vol. 13, Burden & Von Knippenberg, Amsterdam, Elseview, pp. 75–83, 1984

Chiswell & Clackson, 1992

Chiswell & McCafferty, "Phage antibodies: will new 'coliclonal' antibodies replace monoclonal antibodies?" *TIBTECH*, 10:80–84, 1992

Chou & Fasman, "Prediction of protein conformation," *Biochemistry*, 13 (2):222–245, 1974a Chou & Fasman, "Conformational Parameters for Amino Acids in Helical, β-Sheet, and Random Coil Regions Calculated from Proteins," *Biochemistry*, 13 (2):211–222, 1974b Chou & Fasman, "Prediction of the Secondary Structure of Proteins from Their Amino Acid Sequence," *Adv. Enzymol. Relat. Areas Mol. Biol.*, 47:45–148, 1978a Chou & Fasman, "Empirical Predictions of Protein Conformation," *Ann. Rev. Biochem.*, 47:251–276, 1978b Chou & Fasman, "Prediction of β-Turns," *Biophys. J.*, 26:367–384. 1979

Clackson et al., "Making antibody fragments using phage display libraries," *Nature*, 352:624–628, 1991

Francisco et al., *Proc. Natl. Acad. Sci. USA*, 89:2713–2717, 1992

Francisco et al., "Production and fluorescence-activated cell sorting of *Escherichia coli* expressing a functional antibody fragment on the external surface," *Proc. Natl. Acad. Sci. USA*, 90:10444–10448, 1993

Frohman, In: *PCR Protocols: A Guide to Methods and Applications*, Academic Press, N.Y., 1990

Gefter et al., *Somatic Cell Genet.*, 3:231–236, 1977

Georgiou, G. et al, "folding and Aggregation of TEM β-lactamase: Analogies with the Formation of Inclusion Bodies in *Escherichia coli*", *Protein Science*, 3:1953–60 (1994)

Goding, in: *Monoclonal Antibodies: Principles and Practice*, 2nd Ed., Orlando, Fla., Academic Press pp. 60–61, 65–66, 71–74, 1986

Harlow & Lane (Eds.), *Antibodies: A Laboratory Manual*, Cold Spring Harbor Laboratory Press, Cold Spring Harbor, N.Y., 1988

Ho et al., 1989

Huse et al., "Generation of A Large Combinatorial Library of the Immunoglobulin Repertoire in Phage Lambda," *Science*, 246:1275–1281, 1989

Huston, et. al., "Protein engineering of antibody binding sites: Recovery of specific activity in an anti-digoxin single-chain Fv analogue produced in *Escherichia coli*," *Proc. Natl. Acad. Sci. USA*, 85:5879–5883, 1988

Huston et al., 1989

Huston et al., *Methods in Enzymology*, "Molecular Design and Modeling: Concepts and Applications," Abelson & Simon, Academic Press, Inc., San Diego, pp. 46–99, 1991

Innis et al., *PCR Protocols*, Academic Press, Inc., San Diego Calif, 1990

Iverson et al., "A Combinatorial System for Cloning and Expressing the Catalytic Antibody Repertoire in *Escherichia coli*," *Cold Spring Harbor Symposia on Quantitative Biology*, 54:273–281, 1989

Jameson & Wolf, "The Antigenic Index: A Novel Algorithm for Predicting Antigenic Determinants," *Comput. Appl. Biosci*, 4 (1):181–186, 1988

Kabat et al., *Sequences of Proteins of Immunological Interest*, U.S. Dept. of Health and Human Services, U.S. Government Printing Office, 1987

Kang et al., "Linkage of recognition and replication functions by assembling combinatorial antibody Fab libraries along phage surfaces," *Proc. Natl. Acad. Sci. USA*, 88:4363–4366, 1991

Kohler & Milstein, *Nature*, 256:495–497, 1975

Kohler & Milstein, *Eur. J. Immunol.*, 6:511–519, 1976

Kornacker & Pugsley, *Mol. Microbiol*, 4:1101–1109, 1990

Kuby, J. "Immunology", W. H. Freeman and Co., New York (1990)

Kwoh et al., "Transcription-based amplification system and detection of amplified human immunodeficiency virus type 1 with a bead-based sandwich hybridization format," *Proc. Nat. Acad. Sci. USA*, 86:1173–1177, 1989

Lugtenberg & Van Alphen, "Molecular architecture and functioning of the outer membrane of *Escherichia coli* and other gram-negative bacteria," *Bioche m. Biophys. Acta*, 737:51–115, 1983

Maniatis et al., *Molecular Cloning: A Laboratory Manual*, Cold Springs Harbor Laboratories, Cold Springs Harbor, New York, 1982

McCafferty et al., "Phage antibodies: filamentous phage displaying antibody variable domains," *Nature*, 348:552–554, 1990

Morrison & Desrosiers, "A PCR-Based Strategy for Extensive Mutagenesis of a Target DNA Sequence," *BioTechniques*, 14:454–457, 1993

Mullinax et al., "Identification of a human antibody fragment clones specific for tetanus toxoid in a bacteriophage λ immunoexpression library," *Proc. Natl. Acad. Sci. USA*, 87:8095–8099, 1990

Nakamura et al., Enzyme Immunoassays: Heterogeneous and Homogeneous Systems, Ch. 27, 1987

O'Hara, et al., "One-sided polymerase chain reaction: The amplification of cDNA," *Proc. Nat'l Acad. Sci. USA*, 86:5673–5677, 1989

Orlandi et al., "Cloning immunoglobulin variable domains for expression by the polymerase chain reaction," *Proc. Nat. Acad. Sci. USA*, 86:3833–3837, 1989

Parmley & Smith, "Antibody-selectable filamentous fd phage vectors: affinity purification of target genes," *Gene*, 73:305–318, 1988

Persson et al., "Generation of diverse high-affinity human monoclonal antibodies by repertoire cloning," *Proc. Natl. Acad. Sci. USA*, 88:2432–2436, 1991

Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA*, 86:5728–5732, 1989

Schildbach et al., *Protein Science*, 2:206–214, 1993

Scott & Smith, "Searching for Peptide Ligands with an Epitope Library," *Science*, 249:386–390, 1990

Skerra & Plückthun, "Assembly of a Functional Immunoglobulin $F_v$ Fragment in *Escherichia coli*," *Science*, 240:1038–1041, 1988

Smith, 1991

Smith et al., 1992

Smith, 1993

Tanke & van der Keur, *Trends Biotechnol.*, 11:55–62, 1992

Valax & Georgiou, 1992

Walker et al., "Isothermal in vitro amplification of DNA by a restriction enzyme/DNA polymerase system," *Proc. Nat'l Acad. Sci. USA*, 89:392–396, 1992

Winter & Milstein, "Man-made antibodies," *Nature*, 349:293–299, 1991

Wolf et al., "An Integrated Family of Amino Acid Sequence Analysis Programs," *Comput. Appl. Biosci.*, 4 (1):187–191, 1988

Wu et al., "The Ligation Amplification Reaction (LAR)—Amplification of Specific DNA Sequences Using Sequential Rounds of Template-Dependent Ligation," *Genomics*, 4:560–569, 1989

Yang et al., "Electrochemiluminescence: A New Diagnostic and Research Tool," *Bio/Technology*, 12:193–194, 1994

---

What is claimed is:

1. A method for binding an analyte, comprising the steps of:
   (a) obtaining a host cell that expresses from a vector within said host cell an anti-analyte antibody or analyte-combining antibody fragment on the surface of the host cell; and
   (b) contacting said host cell with a sample suspected of containing an analyte that binds to said anti-analyte antibody or analyte-combining antibody fragment under conditions effective to allow the formation of an antibody/analyte complex.

2. The method of claim 1, further defined as a method for removing an analyte from a sample, the method comprising contacting said host cell with a sample containing an unwanted analyte and obtaining the sample free from said complexed analyte.

3. A method for binding an analyte, comprising the steps of:
   (a) obtaining a gram negative bacterial host cell that expresses from a vector within said host cell, an anti-analyte antibody or analyte-combining antibody fragment on the surface of the host cell; and
   (b) contacting said host cell with a sample suspected of containing an analyte that binds to said anti-analyte antibody or analyte-combining antibody fragment under conditions effective to allow the formation of an antibody/analyte complex.

4. The method of claim 3, further defined as a method for removing an analyte from a sample, the method comprising contacting said host cell with a sample containing an unwanted analyte and obtaining the sample free from said complexed analyte.

* * * * *